(12) United States Patent
Scherz et al.

(10) Patent No.: US 7,045,117 B2
(45) Date of Patent: May 16, 2006

(54) METHOD FOR TUMOR DIAGNOSIS COMPRISING ADMINISTERING OF PALLADIUM-SUBSTITUTED BACTERIOCHLOROPHYLL DERIVATIVES

(75) Inventors: Avigdor Scherz, Rehovot (IL); Yoram Salomon, Rehovot (IL); Alexander Brandis, Rehovot (IL); Hugo Scheer, Blonhofen (DE)

(73) Assignee: Yeda Research and Development Co. Ltd., Rehovot (IL)

( * ) Notice: Subject to any disclaimer, the term of this patent is extended or adjusted under 35 U.S.C. 154(b) by 434 days.

(21) Appl. No.: 10/414,007

(22) Filed: Apr. 16, 2003

(65) Prior Publication Data

US 2003/0211044 A1    Nov. 13, 2003

Related U.S. Application Data

(62) Division of application No. 09/857,772, filed as application No. PCT/IL99/00673 on Dec. 9, 1999, now Pat. No. 6,569,846.

(30) Foreign Application Priority Data

Dec. 9, 1999    (IL) ...................................... 133253

(51) Int. Cl.
*A61B 49/00* (2006.01)

(52) U.S. Cl. ........................ 424/9.61; 424/9.6; 424/9.1

(58) Field of Classification Search ............... 424/9.61, 424/9.6, 9.1; 540/145; 514/185
See application file for complete search history.

(56) References Cited

U.S. PATENT DOCUMENTS

| 5,171,741 A | 12/1992 | Dougherty |
| 5,314,905 A | 5/1994 | Pandey et al. |
| 5,726,169 A | 3/1998 | Scherz et al. |
| 6,333,319 B1 | 12/2001 | Scherz et al. |

*Primary Examiner*—Michael Hartley
(74) *Attorney, Agent, or Firm*—Browdy and Neimark, PLLC

(57) ABSTRACT

Palladium-substituted Bacteriochlorophyll derivatives are administered to a subject suspected of having a tumor and the patient is then irradiated and the fluorescence of the suspected area is measured. A high fluorescence indicates a tumor site. A preferred derivative is Pd-Bacteriopheophorbide a.

3 Claims, 11 Drawing Sheets

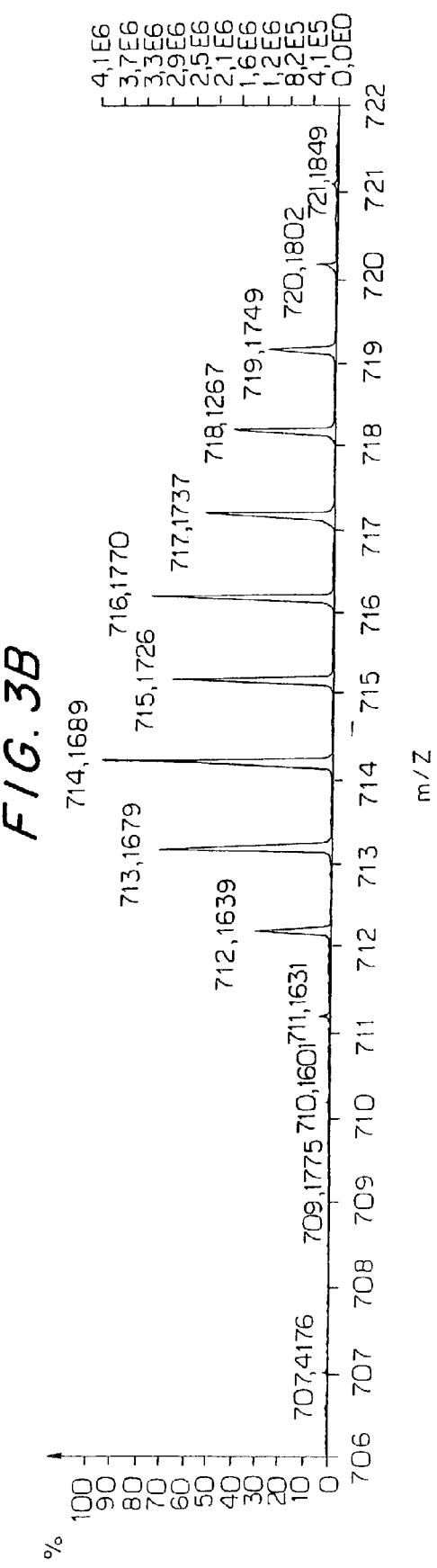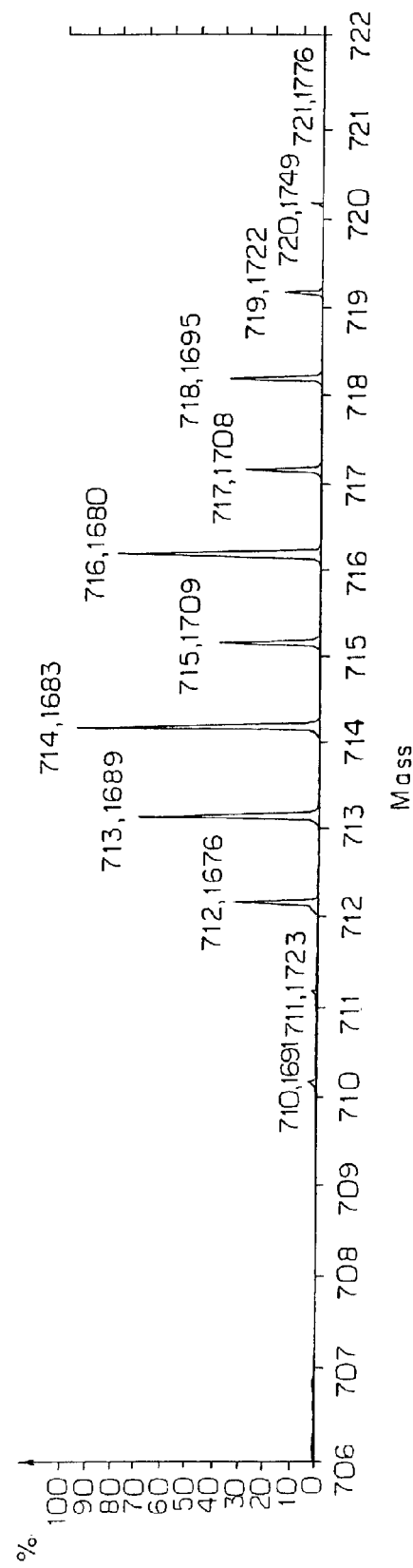

─■─ Dark, Pd-Bpheid
─●─ Dark, Pd-Bpheid-ethyl ester
─◆─ Light, Pd-Bpheid
─▲─ Light, Pd-Bpheid-ethyl ester

BEFORE PDT     1 DAY     5 DAYS

BEFORE PDT     1 DAY     5 DAYS

METHOD FOR TUMOR DIAGNOSIS COMPRISING ADMINISTERING OF PALLADIUM-SUBSTITUTED BACTERIOCHLOROPHYLL DERIVATIVES

CROSS-REFERENCE TO RELATED APPLICATIONS

The present application is a divisional application of U.S. application Ser. No. 09/857,772, filed Sep. 19, 2001 now U.S. Pat. No. 6,569,846, which is the national stage under 35 U.S.C. 371 of international application PCT/IL99/00673, filed Dec. 9, 1999 which designated the United States, and which international application was published under PCT Article 21(2) in the English language.

BACKGROUND OF THE INVENTION

Field of the Invention

The present invention concerns palladium-substituted bacteriochlorophyll derivatives, processes and intermediates for their preparation and pharmaceutical compositions comprising the same as well as their use in the field of in vivo photodynamic therapy and diagnosis and in vitro photodynamic killing of viruses and microorganisms.

Definitions and Abbreviations

BChl=bacteriochlorophyll a (Mg-containing 7, 8, 17, 18-tetrahydroporphyrin having a phytyl or geranylgeranyl group at position $17^3$, a $COOCH_3$ group at position $13^2$, an H atom at position $13^2$, an acetyl group at position 3 and an ethyl group at position 8).

BChlide=bacteriochlorophyllide a (the $C-17^2$-free carboxylic acid derived from BChl a).

BPhe=bacteriopheophytin a (BChl in which the central Mg atom is replaced by two H atoms).

BPheid=bacteriopheophorbide a (the $C-17^2$-free carboxylic acid derived from BPhe).

Pd-BPheid=Pd-bacteriopheophorbide a (the $C-17^2$-free carboxylic acid derived from BPhe having a central Pd atom, a $COOCH_3$ group at position $13^2$, an H atom at position $13^2$, an acetyl group at position 3 and an ethyl group at position 8).

IUPAC numbering of the bacteriochlorophyll derivatives is used throughout the specification. Using this nomenclature, the natural bacteriochlorophylls carry two carboxylic acid esters at positions $13^2$ and $17^2$, however they are esterified at positions $13^3$ and $17^3$.

There has been an increasing interest in the utilization of photosensitizers for cancer therapy. According to this technique, known as photodynamic therapy (PDT), photosensitizers are applied for example to a tumor and the in situ photosentization produces compounds which intoxicate the malignant cells.

Photodynamic therapy using porphyrins and related compounds has, by now, a fairly long history. Early work, in the 1940s, demonstrated that porphyrin could be caused to fluoresce in irradiated tumor tissue. The porphyrins appeared to accumulate in these tissues, and were capable of absorbing light in situ, providing a means to detect the tumor by the location of the fluorescence. A widely used preparation in the early stages of photodynamic treatment both for detection and for therapy was a crude derivative of hematoporphyrin, also called hematoporphyrin derivative, HpD, or Lipson derivative prepared as described by Lipson and coworkers in *J Natl Cancer Inst* (1961) 26:1–8. Considerable work has been done using this preparation, and Dougherty and coworkers reported the use of this derivative in treatment of malignancy (*Cancer Res* (1978) 38:2628–2635; *J Natl Cancer Inst* (1979) 62:231–237).

Dougherty and coworkers prepared a more effective form of the hematoporphyrin derivative which comprises a portion of HpD having an aggregate weight >10 kd. This form of the drug useful in photodynamic therapy is the subject of U.S. Pat. No. 4,649,151, is commercially available, and is in clinical trials.

The general principles of the use of light-absorbing compounds, especially those related to porphyrins, has been well established as a treatment for tumors when administered systematically. The differential ability of these preparations to destroy tumor, as opposed to normal tissue, is due to the homing effect of these preparations to the objectionable cells. (See, for example, Dougherty, T. J., et al., "Cancer: Principles and Practice of Oncology" (1982), V. T. de Vita, Jr., et al., eds. pp 1836–1844.). Efforts have been made to improve the homing ability by conjugating hematoporphyrin derivative to antibodies. (See, for example, Mew, D., et al., *J Immunol* (1983) 130:1473–1477.). The mechanism of these drugs in killing cells seems to involve the formation of singlet oxygen upon irradiation (Weishaupt, K. R., et al., *Cancer Research* 36:2326–232: (1976)).

The use of hematoporphyrin derivative or its active components in the treatment of skin diseases using topical administration has also been described in U.S. Pat. No. 4,753,958. In addition, the drugs have been used to sterilize biological samples containing infectious organisms such as bacteria and virus (Matthews, J. L., et al., *Transfusion* 28:81–83 (1988)). Various other photosensitizing compounds have also been used for this purpose, as set forth, for example, in U.S. Pat. No. 4,727,027.

In general, the methods to use radiation sensitizers of a variety of structures to selectively impair the functioning of biological substrates both in vivo and in vitro are understood in the art. The compounds useful in these procedures must have a differential affinity for the target biological substrate to be impaired or destroyed and must be capable of absorbing light so that the irradiated drug becomes activated in a manner so as to have a deleterious effect on the adjacent compositions and materials.

Because it is always desirable to optimize the performance of therapeutics and diagnostics, variations on the porphyrin drugs traditionally used in treatment and diagnosis have been sought. A number of general classes of photosensitizers have been suggested including phthalocyanines, psoralen-related compounds, and multicyclic compounds with resonant systems in general. Most similar to the compounds disclosed herein are various pheophorbide derivatives whose use in photodynamic therapy has been described in EPO Application 220686 to Nihon Metaphysics Company; ethylene diamine derivatives of pheophorbide for this purpose described in Japanese Application J85/000981 to Tama Seikayaku, K. K., and Japanese Application J88/004805 which is directed to 10-Hydroxypheophorbide-a. In addition, Beems, E. M., et al., in *Photochemistry and Photobiology* 46:639–643 (1987) disclose the use as photosensitizers of two derivatives of bacteriochlorophyll-a—bacteriochlorophyllin-a (also known as bacteriopheophorbide-a, which lacks the phytyl alcohol derivatized in bacteriochlorophyll-a) and bacteriochlorin-a (which lacks both the phytyl group and the Mg ion). These authors direct their attention to these derivatives as being advantageous on the grounds of enhanced water solubility as compared to bacteriochlorophyll-a.

EP 584552 and WO97/19081, both to Yeda Research and Development Co. Ltd., describe chlorophyll and bacteriochlorophyll derivatives and their use as PDT agents, and metaled bacteriochrophylls and their preparation by transmetalation of the corresponding Cd—BChl derivatives, respectively.

The problem remains to find suitable photosensitizers useful in photodynamic therapy and diagnosis which are optimal for particular targets and particular contexts. Thus, the invention provides an additional group of photosensitizing compounds which becomes part of the repertoire of candidates for use in specific therapeutic and diagnostic situations.

SUMMARY OF THE INVENTION

It has now been found, in accordance with the present invention, that the compounds of formula I, I' or I" below wherein A as defined below represents a substituent capable of allowing an efficient plasma transfer and cell membrane penetration, are useful as PDT agents and present the advantages of enhanced solubility, stability and/or efficiency, compared with the known compounds.

The invention thus concerns the compounds of formula I, I' or I"

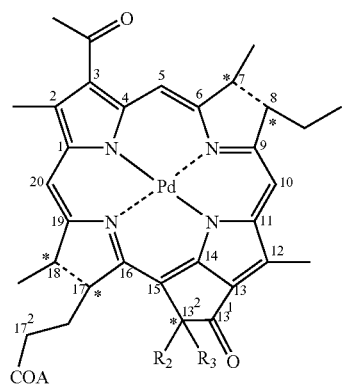

I

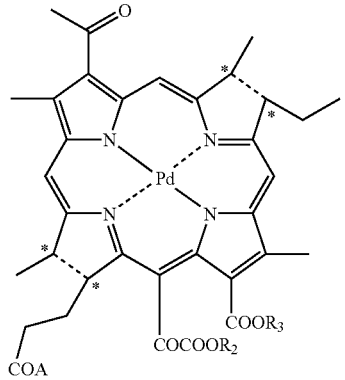

I'

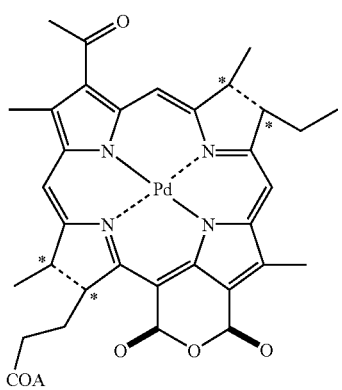

I"

wherein

A represents OH,

OR$_1$,

—O—(CH$_2$)$_n$—Y,

—S—(CH$_2$)$_n$—Y,

—NH—(CH$_2$)$_n$—Y,

—O—(CH$_2$)$_2$—NH$_2$,

—O—(CH$_2$)$_2$—OH,

—NH—(CH$_2$)$_n$—$^+$N O, X$^-$,

—NH—(CH$_2$)$_2$—NH—BOC or

—N—(CH$_2$—CH═CH$_2$)$_2$ wherein

R$_1$ represents Na$^+$, K$^+$, (Ca$^{2+}$)$_{0.5}$, (Mg$^{2+}$)$_{0.5}$, Li$^+$, NH$_4$$^{++}$ NH$_3$—C (CH$_2$OH)$_3$, $^+$NH$_3$—CH$_2$—(CHOH)$_4$—CH$_2$OH, $^+$NH$_2$(CH$_3$)—CH$_2$—(CHOH)$_4$—CH$_2$OH or $^+$N(C$_n$, H$_{2n'+1}$)$_4$;

R$_2$ represents H, OH or COOR$_4$, wherein R$_4$ is C$_1$–C$_{12}$ alkyl or C$_3$–C$_{12}$ cycloalkyl;

R$_3$ represents H, OH or C$_1$–C$_{12}$ alkyl or alkoxy;

n is 1, 2, 3, 4, 5 or 6,

Y is —NR'$_1$R'$_2$ or —$^+$NR'$_1$R'$_2$R'$_3$, X$^-$ wherein R'$_1$, R'$_2$ and R'$_3$ independently from each other represent —CH$_3$ or —C$_2$H$_5$;

X is F, Cl, Br or I, n' is 1, 2, 3 or 4, and wherein * denotes an asymmetric carbon and— represents a single saturated bond or a double unsaturated bond.

Furthermore, the present invention concerns processes for the preparation of the above new compounds.

Thus, in one aspect, it is herein described a method to effect the impairment or destruction of a target biological substrate which method comprises treating the target substrate with an amount of the compound of formula I, I' or I" effective to photosensitive said substrate followed by irradiating said target substrate with radiation in a wavelength band absorbed by the compound of formula I, I' or I" for a time effective to impair or destroy the substrate.

In other aspect, the invention is therefore directed to pharmaceutical compositions comprising at least a compound of formula I, I' or I" as an active agent, together with a pharmaceutically acceptable carrier. The compositions are useful for in vivo photodynamic therapy and diagnosis of tumors and for killing of cells, viruses and bacteria, parasites and fungi in samples and in living tissues by well-known photodynamic techniques.

Furthermore, the invention concerns the use of the compounds of formula I, I' or I" for the preparation of a pharmaceutical composition useful in photodynamic therapy.

The invention further concerns the use of the invention compounds for the preparation of compositions useful in diagnosis and ex vivo killing of bacteria, parasites, viruses and fungi.

The invention further concerns the acid chloride and anhydride of formulas II and III herebelow, respectively, as intermediates.

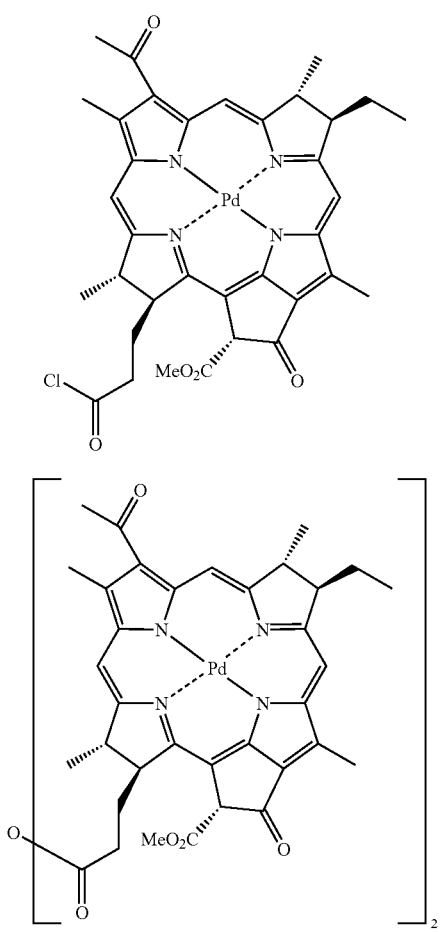

DETAILED DESCRIPTION OF THE INVENTION

Figure 1:
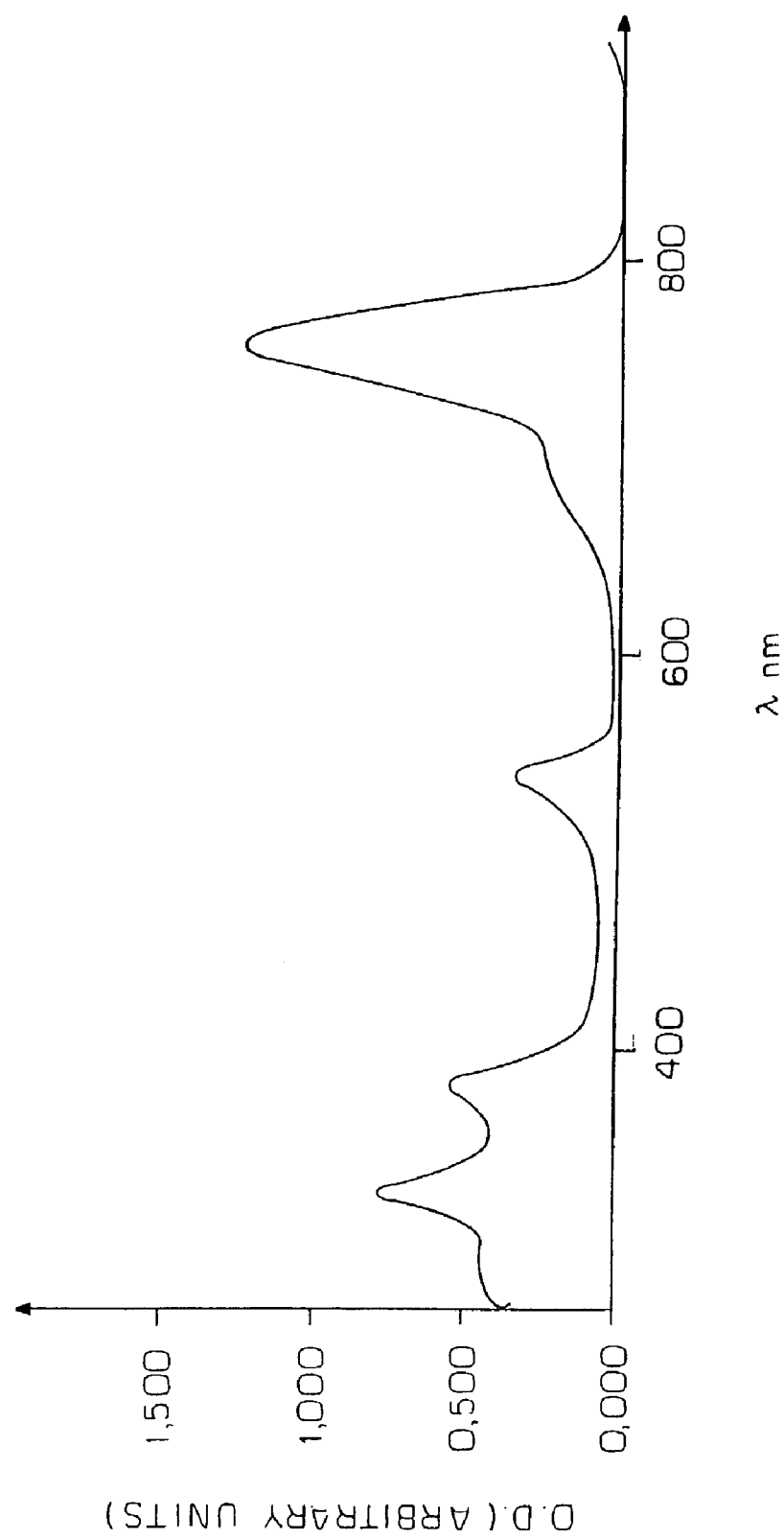
FIG. 1 depicts the optical absorption spectrum of Pd-BPheid in a mixture of acetone and methanol/K buffer phosphate.

In a preferred embodiment, the compounds of the invention have the following formula with the optical configuration below:

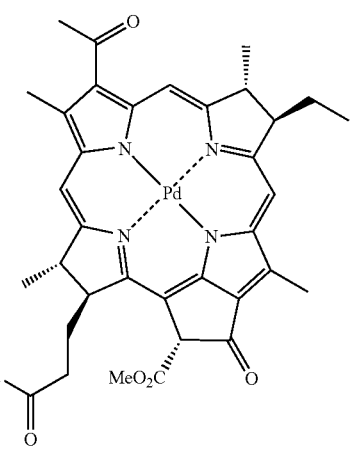

wherein A is as above.

When the dotted lines representing the bond between C7 and C8 and C17 and C18 in the above structure is a saturated single bond, the carbon atoms numbered 7, 8, 17 and 18 are asymmetric carbon atoms. When $R_2$ or $R_3$ is H, $C13^2$ is an asymmetric carbon atom.

In the presence of oxygen or at the ambient air and under light action, the oxidation of the above C7–C8 and C17–C18 bonds may occur, resulting in compounds with double bo at said positions C7–C8 and C17–C18.

The compounds of formula I' and I" of the present invention are oxidized forms of the compounds of formula I and can be obtained by the processes described in *Chlorophyll*, by Scheer H. (ed.), CRC Press, 1991, pp. 147–209.

In a preferred embodiment of the invention, the compounds are those wherein A is $OR_1$.

In a most preferred embodiment, the compound of the invention is Pd-PBheid (also designated herein sometimes Pd-BChl-COOH), the compound of formula I wherein A is OH, having the following structure:

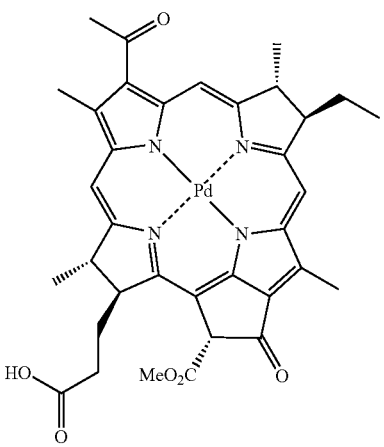

One of the processes for the preparation of the compounds of formula I wherein A is OH, comprises at least the steps of:
a) combined demetalation and hydrolysis of a M-BPheid-$17^3$-Z compound wherein Z is phytyl, geranylgeranyl (gg) or SerOMe (seryl O-methyl ester) and M is a metal selected from Mg, Cd, or Zn;
b) incorporation of Pd with a Pd reagent into the compound obtained in (a), thus obtaining a Pd-BPheid, and, if desired,
c) subsequent reaction of the obtained Pd-BPheid with a corresponding compound of formula A-H, wheren A is other than OH for forming the corresponding $R_1$ salt or a compound wherein A is not OH.

In one preferred embodiment, the process is directed to the preparation of Pd-BPheid and bacteriochlorophyll a (Bchla) is demetalated and hydrolyzed in step (a), and the obtained bacteriopheophorbide (BPheid) is reacted with a Pd reagent in step (b) to produce the desired Pd-BPheid.

Another process for the preparation of the compound of formula I comprises at least the steps of:
a) transmetalation of a BChlide-$17^3$-Z to obtain the corresponding Pd- BPheid-$17^3$-Z wherein Z is phytyl, gg or Ser OMe,
b) hydrolysis of the obtained compound, and
c) optionally subsequent reaction of the obtained Pd-BPheid with a corresponding compound of formula $R_1$—H or A-H for forming the corresponding $R_1$ salt or a compound wherein A is not OH.

In one preferred embodiment, the process is directed to the preparation of Pd-BPheid and bacteriochlorophyll a (Bchla) is transmetalated in step (a) to replace the native central Mg atom by Pd, and the obtained Pd-BPheid-$17^3$-Z wherein Z is phytyl is hydrolized in step (b) to produce the desired Pd-BPheid.

Another process for the preparation of the compound of formula I comprises at least the steps of:
a) enzymatic hydrolysis of a BChlide-$17^3$-Z wherein Z is phytyl or geranylgeranyl to obtain a Bchlide;
b) acidic demetalation of said BChlide of (a);
c) incorporation of Pd with a Pd reagent into the demetalated BPheid of (b); and
d) optionally subsequent reaction of the obtained Pd-BPheid with a corresponding compound of formula A-H, wherein A is other than OH, for forming the corresponding $R_1$ salt or a compound wherein A is not OH.

In the above processes for the preparation of compounds of formula I, the Pd reagent may be any convenient reactive compound providing Pd in such structures such as, for instance, Pd acetate and Pd chloride.

The incorporation of Pd in the procedures above can be achieved by a two-step procedure using Na ascorbate or ascorbic acid, or by a one-step procedure using 6-O-palmitoyl-L-ascorbic acid.

The compounds of the invention wherein A is different from OH and $OR_1$ may be obtained by reaction of the Pd-BPheid (Pd—BChl-COOH) with the corresponding A-H compound.

The compounds of formula II and III above are intermediates for the compounds of formula I of the invention. The acid chlorides of formula II, Pd-BPheid-COCl, may be obtained by using any agent suitable for forming acyl chlorides, such as for example $SOCl_2$.

The acid anhydrides of formula III may be obtained by dehydration of the compounds of formula I, I', I'' with acetic anhydride.

By reaction of these intermediates II and III with the corresponding compound AH, the compounds of formula I, I' or I'' may be obtained.

The invention further comprises pharmaceutically acceptable salts of the free acids of formulas I, I' and I''. The salts can be formed by methods well known in the art such as by reaction of the free acid or a salt thereof with inorganic or organic reagents such as, but not limited to, NaOH, KOH, calcium or magnesium suitable salts, LiOH, $NH_4OH$, tetraalkylammonium hydroxide, e.g., tetraethylammonium hydroxide, or N-methylglucamine, glucamine and triethanolamine.

The compounds of the invention are for use in photodynamic therapy and diagnosis with respect to target biological substrates. By "target biological substrate" is meant any cells, viruses or tissues which are undesirable in the environment to which therapy or other corrective action, such as sterilization, is employed, or the location of which is desired to be known in an environment to which diagnosis is applied.

According to the present invention, the drug is injected into the subject, and permitted to reach an optimal concentration in the target substrate. Then the target substrate is exposed to radiation at a wavelength appropriate to the absorption spectrum of the compound administered. The effect of the compound can be enhanced by concomitant increase of the target substrate temperature.

For use in the method of the invention, the compounds of the invention are formulated using conventional excipients appropriate for the intended use. For systemic administration, in general, buffered aqueous compositions are employed, with sufficient nontoxic detergent to solubilize the active compound. As the compounds of the invention are generally not very soluble in water, a solubilizing amount of such detergent may be employed. Suitable nontoxic detergents include, but are not limited to, Tween-80, various bile salts, such as sodium glycholate, various bile salt analogs such as the fusidates. Alternate compositions utilize liposome carriers. The solution is buffered at a desirable pH using conventional buffers such as Hank's solution, Ringer's solution, or phosphate buffer. Other components which do not interfere with the activity of the drug may also be included, such as stabilizing amounts of proteins, for example, serum albumin, or low density- or high density-lipoprotein (LDL and HDL, respectively).

Systemic formulations can be administered by injection, such as intravenous (i.v.), intraperitoneal (i.p.), intramuscular, or subcutaneous (s.c.) injection, or can be administered by transmembrane or transdermal techniques. Formulations appropriate for transdermal or transmembrane administration include sprays and suppositories containing penetrants, which can often be the detergents described above.

For topical local administration, the formulation may also contain a penetrant and is in the form of an ointment, salve, liniment, cream, or oil. Suitable formulations for both systemic and localized topical administration are found in *Remington's Pharmaceutical Sciences*, latest edition, Mack Publishing Co., Easton, Pa.

For use ex vivo to treat, for example, blood or plasma for transfusion or preparations of blood products, no special formulation is necessary, but the compounds of the invention are dissolved in a suitable compatible solvent and mixed into the biological fluid at a suitable concentration, typically of the order of 1–100 µg/ml prior to irradiation.

For photodynamic therapeutic and diagnostic applications, suitable dosage ranges will vary with the mode of application and the choice of the compound, as well as the nature of the condition being treated or diagnosed. However, in general, suitable dosages are of the order of 0,01 to 50 mg/kg body weight, preferably 0,1 to 10 mg/kg. For topical administration, typically amounts on the order of 5–100 mg total are employed.

The general procedures for photodynamic ex vivo treatment are analogous to those described by Matthews, J. L., et al., *Transfusion* (supra).

Briefly, for systemic administration, a suitable time period after administration, typically from several minutes to two days is allowed to elapse in order to permit optimal concentration of the compounds of the invention in the target biological substrate. In general, this substrate will be a tumor vasculature, tumor cells or any other tumor component, and the localization of the compound can be monitored by measuring the optical absorption of the target tissue as compared to background. After optimization has been accomplished, the target biological substrate is irradiated with a suitable band of irradiation, in the range of 740–800 nm, or 500–600 nm or 700–900 nm at a rate of 5–750 mW/cm$^2$, and a total energy of 100–1000 J/cm$^2$.

For topical treatment, localization is immediate, and the corresponding radiation can be provided thereafter. For treatment of biological fluids ex vivo, radiation is applied after optimal binding/uptake by the target tissue is reached. The radiation fluence is on the order of 1–10 J/cm$^2$. Because penetration of tissue is not required, lower total energy can be employed.

The compositions of the invention comprise at least one compound of formula I, I' or I" as defined above together with a physiologically acceptable carrier. These compositions may be in the form of a solution, a lipid emulsion or a gel or in the form of liposomes or nanoparticles. The suitable carrier is chosen to allow optimization of the concentration of the compound of the invention at the target substrate. Examples of such carriers, but not limited to, are "Tween 80", polyethyleneglycol, e.g., PEG400, "Cremophor EL", propylene glycol, ethanol, basil oil, bile salts and bile salts analogs and mixtures thereof. Liposome formulations can be based, for example, on dimyristoylphosphatidyl choline or phosphatidyl glycerol. The carrier may also comprise dipalmitoylphosphatidyl choline.

When nanoparticles are used, they may be in the form of PEG-coated poly(lactic acid) nanoparticles. In the form of lipid emulsions, low density lipoproteins and triglycerides are usually used.

In the composition of the invention, the invention compound(s) is (are) in an amount of 0.01 to 20%, preferably 0.05% to 5% by weight of the total weight composition.

The invention will now be illustrated by the following non-limiting examples.

EXAMPLES

Example 1

Preparation of Pd-BPheid

Pd-BPheid was prepared from BChla by the following 3-step procedure.

(a) Isolation of Bacteriochlorophyll a (BChla)

BChla was extracted form lyophilized bacteria *Rhodovolum sulfidophilum* as follows:

Lyophilized cells (100 gr) were ground to powder, washed 5 times with a total of 1250 ml acetone to partially wash away the carotenoids, the mixture was filtered and BChla was extracted from the solid with absolute methanol (≈1200 ml, 4–5 filtrations). After filtering, the dark blue-green solution was partly evaporated under vacuum, the concentrated solution (≈500 ml) was extracted 2–3 times with petrol ether (b.p. 80–100° C., ≈1300 ml) to further eliminate carotenoids, and the petrol ether phase was extracted twice with methanol (≈550 ml). This phase was then discarded, the combined methanol phase was evaporated under vacuum, and the blue-green residue was redissolved in methanol-acetone (1:3, v/v) and loaded on a DEAE-Sepharose column (3×10 cm) equilibrated with methanol-acetone (1:3, v/v). The BChla was eluted with methanol-acetone (1:3, v/v), the methanol-acetone mixture was evaporated and the dry Bchla was redissolved in an exact volume (for absorption spectrum) of ether and filtered through cotton wool to get rid of dissolved column material. After a final evaporation the solid pigment was stored under Argon in the dark at –20° C. Extraction yield: about 700 mg BChla per 100 g lyophilized cells.

The DEAE-Sepharose column was prepared as previously described (Omata and Murata, 1983, "Preparation of Chlorophyll a, Chlorophyll b and Bacteriochlorophyll a by column chromatography with DEAE-Sepharose C1-6B and Sepharose C1-6B", *Plant Cell Physiol* 24:1093–1100). Briefly, DEAE-Sepharose was washed with distilled water and then converted to an acetate form by suspending it in a 1M sodium acetate buffer (pH=7). The slurry was washed 3 times with acetone and finally suspended in methanol-acetone (1:3, v:v) for storage at 5° C.

(b) Preparation of Bacteriopheophorbide (BPheid)

Crude Bchla extract as obtained in (a) (about 100 mg Bchla containing some residual carotenoides) was dissolved in 80% aqueous trifluoroacetic acid (about 15 ml) which had been bubbled with nitrogen for 10 min. The solution was stirred at ambient temperature for 2 h. Then the reaction mixture was poured into water (250 ml) and extracted with chloroform. The extract was washed twice with water and dried over anhydrous $Na_2SO_4$. After evaporation of the solvent the residue was chromatographed on Silica (3 cm×15 cm column, Kieselgel 60, Merck) and eluted with methanol in chloroform by step gradient: 2%, 5%, 10%, 15%. At the beginning, carotenoids and a small amount of bacteriopheophytin were washed out, followed by elution of allo-bacteriopheophytin and carotenoids. At 10% methanol in chloroform the product started to be collected and monitored by TLC (Kieselgel, chloroform-methanol, 9:1). The product (60 mg) was evaporated, and the residue taken up in $CHCl_3$ was filtered through UltraPore membrane to remove residual silica that could otherwise cause oxidations.

(c) Incorporation of Palladium into Bacteriopheophorbide (Bpheid)

BPheid (100 mg) as obtained in (b) and Pd-acetate (80 mg) were dissolved in dichloromethane (≈10 ml) and added to a suspension of 200 mg sodium ascorbate in 50 ml of methanol. The reaction mixture was stirred in a closed flask at room temperature, and samples from the reaction mixture were collected every 15–20 minutes and their optical absorption recorded. After about 4 hours, most of the BPheid absorption at 357 nm was replaced by the Pd-BPheid absorption at 330 and 390 nm.

The reaction mixture was transferred into a chlorofom/water solution (200 ml; 50:50 v/v) and shaken in a separatory funnel. The organic phase was collected, washed with water, dried over anhydrous sodium chloride, and evaporated. The dried material was added to 80 mg of Pd-Acetate and steps above were repeated until the residual absorption at 357 nm completely vanished and the ratio between the absorption at 765 nm (the peak of the red-most transition) and the absorption maximum at 330 nm reached the value of ≈2.4 (in chloroform).

The dried reaction mixture was solubilized in a minimal volume of 2:1 chloroform:acetone and loaded on a CM-Sepharose column (150 mm×25 mm) that had been pre-equilibrated with acetone. The column was first washed with acetone and the eluted first fraction was discarded. The column was then washed with 9:1 acetone:methanol. Two bands became prominent and were washed out—the first was the major product and the second was an allomerized by-product (discarded). The product was concentrated almost to dryness and transferred into a 50:50 chloroform:water system in a separatory funnel. The mixture was thoroughly shaken and the organic phase was separated, dried over anhydrous sodium sulfate (or sodium chloride) and evaporated to dryness.

Example 2

Preparation of Pd-BPheid (a) Isolation of Bchla

This step of the procedure was carried out as in Example 1(a) above.

(b) Preparation of Pd-Bpheid

6-O-palmitoyl-L-ascorbic acid (246 mg, 593 µmol) was dissolved in MeOH (84 ml) and $N_2$ was passed through the solution. Bpheid (92 mg, 151 µmol) and $Pd(CH_3COO)_2$ (83 mg, 370 µmol) were dissolved in $CHCl_3$ (34 ml, degassed with $N_2$) and added to the methanolic solution. The mixture was kept under inert atmosphere by stirring and the reaction progress was monitored by recording the absorption spectra of small reaction portions every few minutes. After ~30 min. the reaction was completed and the solvents were evaporated.

(c) Purification of Pd-Bpheid

The crude Pd-BPheid was dissolved in $CHCl_3$ and loaded on a column packed with 15 g of 0.4%-Silica-Asc. Small volume of $CHCl_3$ (~30 m)l was passed through the column and than the pigment was eluted using $MeOH:CHCl_3$ (1:99, ~250 ml). Purity of the fractions was determined by TLC and optical absorption spectroscopy. Mass Spectroscopy and NMR detection were performed on representative samples. Yield: 82.5 mg of pure Pd-BPheid (76%).

For the preparation of the 0.4%-Silica-Asc, ascorbic acid (240 mg) was dissolved in 240 cc of $EtOH:CHCl_3:MeOH$ (60:60:120) mixture. Silica gel 60 (60 g, Merck, Cat. No. 107734, mesh 70–230) was added and the slurry mixture was stirred for 10 min. and then filtered at the pump. The yellowish Silica-Asc. was finally dried for ~1 hr. at ~50° C. This 0.4%-Silica-Asc. is ready to use as regular silica gel; its nature is less polar and it has some antioxidative properties.

Example 3

Preparation of Pd-BPheid (a) Isolation of Bchla

This step was performed as in Example 1(a) above.

(b) Preparation of Chlorophyllase (Chlase)

Chlorophyllase (Chlase) was prepared from chloroplasts of *Melia azedarach L.*, Chine tree leafs. Fresh leaves (50 g) were ground for 2 min. in a blender containing 350 ml of acetone cooled to −20° C. The homogenate was filtered through four layers of gauze, and the filtrate was collected and left overnight at 4° C. for further precipitation. The acetone was removed by filtration, and the remaining powder was washed a few times with cold acetone to remove traces of Chlase and carotenoids until the filtrate was colorless. The Chlase acetone powder was finally dried in a lyophilizer and further stored at −20° C. Under these conditions, the enzyme preparation was stable for over 1 year without noticeable loss of activity. Yield: 20 g Chlase per 1 kg leaves were obtained.

(c) Synthesis and Purification of Bacteriochlorophyllide (BChlide)

Ascorbic acid (70 mg; Merck) was dissolved in water (9 ml), the pH of the solution was adjusted to 7.7 using 10 M KOH aqueous solution, and 1 ml of 0.5 M sodium phosphate buffer (pH 7.7) was added to maintain the pH during the reaction. Triton X-100 (about 80 µl) was added to achieve a final detergent concentration of 0.8% (v/v). Chlase acetone powder (200 mg) was homogenized in 6 ml of this solution using a Polytron homogenizer. The remaining solution was used to wash the instrument and was then combined with the homogenate. The enzyme solution was sonicated with 20 mg of solid BChla saturated with Argon and incubated in the dark for 6 hrs at 37° C., while stirring.

For purification, the reaction material was directly frozen (−20° C.) after 6 hrs of reaction and subsequently lyophilized. The dry residue was dissolved in acetone and sonicated and the solution was then subjected to a CM-Sepharose column equilibrated in acetone. The column was washed with acetone to elute unreacted material and then with 5% and 7% methanol (v/v) in acetone to elute Bacteriochlorophyllide (Bchlide) and Bacteriopheophorbide (Bpheid). The product was eluted with 25% methanol in acetone. The solvent was evaporated and the solid pigment was stored under Argon, at −20° C., in the dark. Reaction yield: 30–55%.

The CM-Sepharose for chromatography was prepared by first washing CM-Sepharose with water and then 3 times with acetone before packing a column and equilibrating in acetone. The chromatographic material could be reused after thorough rinsing with 2M NaCl aqueous solution until colorless, washed with water and resuspended in acetone.

(d) Incorporation of Palladium into the Bacteriopheophorbide (BPheid)

The procedure is the same as in Example 1 (c) above. HPLC of the dried material showed the main product in the form of two epimers which were chemically identical (88% of the entire mixture) and residual allomers. There was also a slight (0.5%) contamination of the starting material, BPheid.

Example 4

Characterization of the Compound Pd-BPheid (a) Absorbance Spectra

The absorbance spectra of Pd-BPheid were determined with a UVICON spectrophotometer (1 cm pathlength) using a PM detector which is normalized to baseline. The sensitivity is 0.05.

Absorbance spectra of Pd-Bpheid in acetone and a mixture of methanol/K phosphate buffer are reported in Table 1 and in FIG. 1.

The absorbance spectrum of Pd-BPheid in plasma was red-shifted to 763 nm.

TABLE 1

| | Acetone | | Methanol/K Phosphate 20 mM pH 6.59 (70%/30%) | |
|---|---|---|---|---|
| | λ | Absorbance | λ | Absorbance |
| | 753 nm | 2.43 | 758 nm | 1.25 |
| | 530 nm | 0.49 | 537 nm | 0.324 |
| | 385 nm | 1.25 | 384 nm | 0.535 |
| | 331 nm | 1.45 | 329 nm | 0.777 |

The pic detection revealed the following peaks according to FIG. 1: at 758 nm: 1.2502; at 537 nm: 0.3239; at 384 nm: 0.5351; and at 329 nm: 0.7766.

(b) HPLC Detection of Pd-BPheid

A reverse phase HPLC method was developed to characterize the impurity profile and quantify the Palladium-BPheid.

| | |
|---|---|
| Solid phase | a $C_8$ Inertsil 5 μm, 250 × 4.6 mm |
| Liquid phase | methanol:potassium phosphate buffer 20 mM pH = 6.59 (70%:30%) |
| Flow rate | 1 ml/min |
| Volume of injection | 100 μl |
| Detection | 1-Spectroflow 783, Deuterium lamp: 385 nm |
| | 2-Spectroflow 757, Tungsten lamp: 753 nm |

As shown in Table 2, HPLC analysis of the product Pd-Bpheid as obtained in Example 3 exhibited 7 peaks. The major peak represented 64 to 70% of the total products.

Solutions of Pd-BPheid stored in acetone at −20° C. were stable for at least 2-month period. When the stock solution was maintained at room temperature for 18 hours, no change in the HPLC profile was observed showing that Pd-Bpheid is a stable compound.

TABLE 2

HPLC Detection of Pd-BPheid

| Peak | % Detection 385 nm | % Detection 753 nm | Absorption spectra (wavelength of maxima nm) |
|---|---|---|---|
| B1 | 0.7 | 0.78 | |
| B2 | 3.4 | 4.31 | 754, 537, 384, 330 |
| C | 1.07 | 1.25 | |
| D | 2.49 | 2.76 | 758, 535, 384, 330 |
| E | 64.11 | 69.98 | 758, 537, 384, 329 |
| F | 9.62 | 3.61 | 753, 531, 358 |
| G | 13.56 | 14.46 | 758, 537, 384, 329 |

(c) Characterization of Pd-BPheid by NMR

After a purification step of the Pd-BPheid prepared according to the Example 3, the percentage of the major peak was above 90%. This purification was conducted by a preparative HPLC C8. This purified compound was used for the characterization of the product by NMR and mass spectrometry.

Analysis of Pd-BPheid by NMR was carried out and the chemical shifts are listed in Table 3:

$^1$H NMR and $^{13}$C NMR
$2D^1$H NMR (COSY and NOESY)
$2D^1$H-$^{13}$C NMR (HMQC and HMBC: reverse detection).

TABLE 3

| $^1$H$^{13}$C Chemical Shifts (ppm) | | |
|---|---|---|
| | Proton | Carbon |
| Methyl | | |
| 1-$CH_3$ | 3, 44 | 14, 4 |
| 2-$CH_3$ | 3, 07 | 33, 1 |
| 3-$CH_3$ | 1, 75 | 23, 6 |
| 4-$CH_3$ | 1, 06 | 10, 8 |
| 5-$CH_3$ | 3, 36 | 12, 5 |
| 8-$CH_3$ | 1, 65 | 23, 9 |
| 10-$CH_3$ | 3, 85 | 53, 3 |
| Meso | | |
| α | 9, 11 | 101, 5 |
| β | 8, 50 | 102, 9 |
| δ | 8, 45 | 98, 7 |
| C—H | | |
| 3-H | 4, 35 | 47, 2 |
| 4-H | 4, 09 | 55, 2 |
| 7-H | 4, 10 | 49, 2 |
| 8-H | 4, 34 | 49, 2 |
| 10-H | 5, 92 | 65, 10 |
| Others | | |
| 4-$CH_2$ | 2, 08; 2, 22 | 30, 6* |
| 7'-$CH_2$ | 2, 30; 2, 52 | 30, 6* |
| 7''-$CH_2$ | 2, 15; 2, 35 | 35* |
| Carbon without Proton | | |
| 2-CO | | 199 |
| 9-CO | | 188 |
| 17-$CO_2$H | | 170, 2 |
| 10-$CO_2$Me | | 174, 3 |
| 1-C | | 141 |
| 2-C | | 135, 6 |
| 5-C | | 126, 9 |
| 6-C | | 130, 1 |
| 11-C | | 142, 3 |
| 12-C | | 158, 5 |
| 13-C | | 159, 5 |
| 14-C | | 151, 5 |
| 15-C | | 140, 5 |
| 16-C | | 152, 5 |
| 17-C | | 109, 8 |
| 18-C | | 152, 3 |
| 19-C | | 158, 6 |

(d) Characterization of Pd-BPheid by Mass Spectrometry

Figure 2:
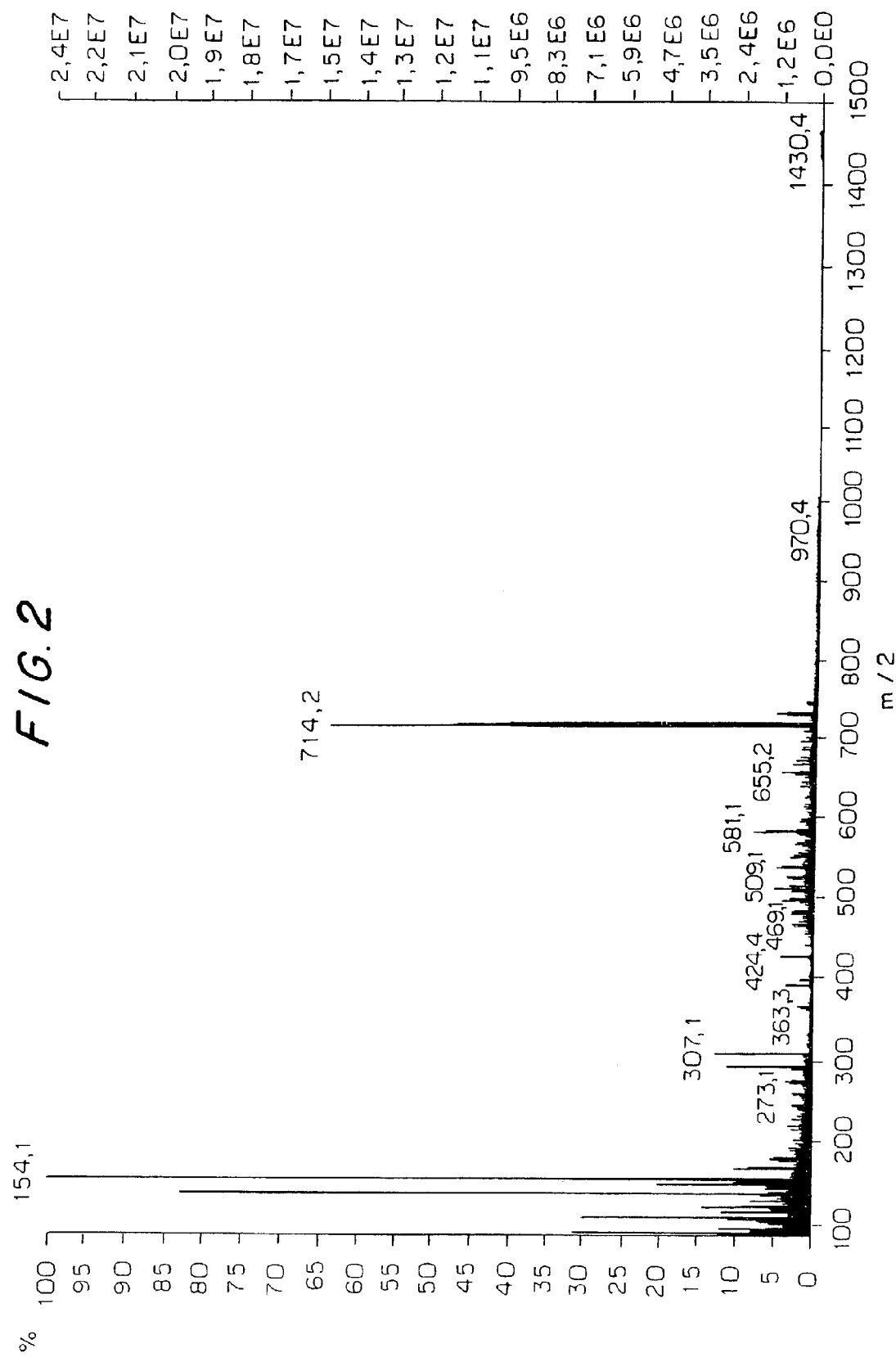
FIGS. 2 and 3 depict, respectively, low and high resolution mass spectra of Pd-BPheid conducted by Fast Atom Bombardement (FAB-MS).
Figure 3A:
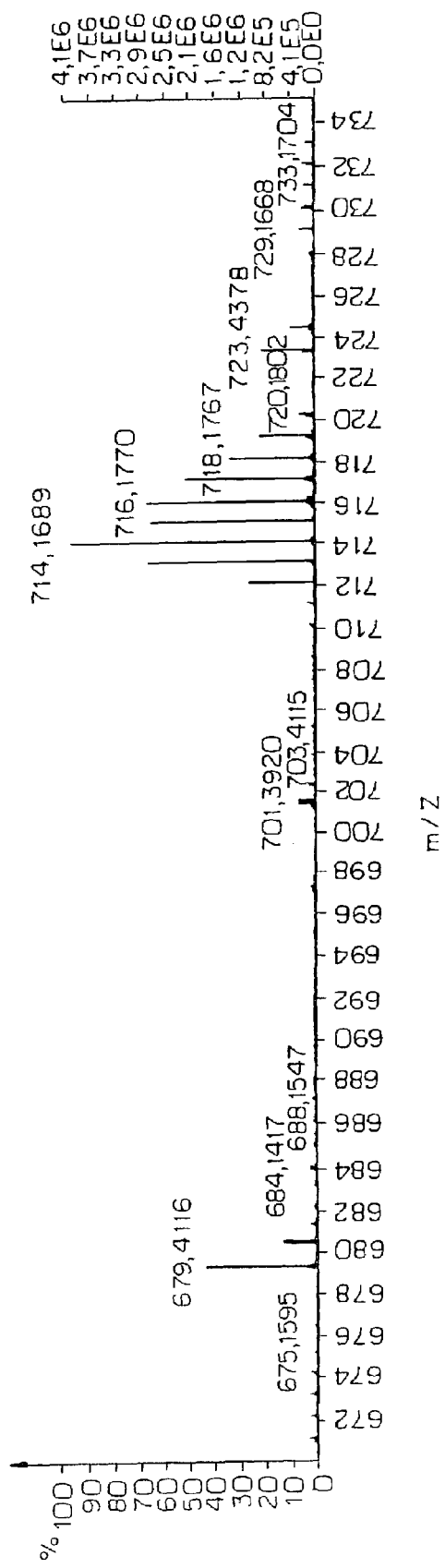

The mass spectrometry analysis of Pd-BPheid resulted in the spectra depicted in FIGS. 2 and 3. It was conducted by Fast Atom Bombardment (FAB) under low and high resolutions. The spectrometer was a "ZabSpec TOF Micromass" spectrometer; ionisation mod: LSIMS with $Cs^+$, positive, acceleration: 8 kV; source temperature: 40° C.; solvent used: mNBA (meta-nitrobenzilic alcohol); input: lateral.

Results: iontype: M+; formula: $C_{35}H_{36}N_4O_6{}^{106}Pd$; theory: 714.1670 Z:1m/z theoretical 714.1670 m/z found 714.1689.

These results confirmed the NMR study: m/e=714 and confirmed the insertion of Palladium metal.

The chemical structure analyzed by NMR and mass spectrometry is the palladium derivative of the free acid form of BChl-Pd-BPheid.

Example 5

Biological Activity of Pd-Bpheid on Murine L1210 and Human ht29 Cells (i) Cell Lines.

The murine leukemia cell line (L1210) was maintained in suspension culture using Fischer's medium supplemented with 10% horse serum, 1 mM glutamine, 1 mM mercaptoethanol and gentamicin. The RIF (Radiation induced Fibrosarcoma) tumor was maintained as specified by Twentyman et al. (1980, "A new mouse tumor model system (RIF-1) for comparison of end-point studies", *J Natl Cancer Inst* 64:595–604). Cultures were grown in Weymouth's medium containing 10 fetal calf serum and gentamycin.

HT29 human colon adenocarcinoma cells were cultured in RPMI 1640 without phenol red and with 10% FCS. Cells were subcultured by dispersal with 0.25% trypsin in 0.02% EDTA and replated at a 1:5 split.

(ii) In Vitro Phototoxicity.

For studies on phototoxicity involving L1210 and RIF cells, light was provided by a 600 watt quartz-halogen source filtered with 10 cm of water and a 850 nm cut-off filter to remove IR. The bandwidth was further confined to 660±5 nm by an interference filter (Oriel). Cells in suspension (L1210) or adhering to 24 mm diameter cover slips were incubated in growth medium (with 20 mM HEPES pH 7 replacing $NaHCO_3$ for added buffering capacity) for 15 min in the presence of specified levels of sensitizers. The cells were then washed free from the sensitizer, and transferred to fresh media. Irradiations were carried out at 10° C. For some studies, the cells were then labeled with fluorescent probes and sites of photodamage were assessed. In other studies, the cells were then incubated for 60 min at 37° C. in fresh medium to allow apoptosis to proceed. Viability studies were carried out using 96-well plates and a 72-hour MTT assay, in quadruplicate.

For HT29 model, cells were incubated for 1 hour with different concentrations of Pd-Bpheid and irradiated by an halogen lamp or a titanium sapphire laser with 300 mW/$cm^2$ at 10 and 25 J/$cm^2$.

(iii) Cell Viability.

Cell survival was assessed by the MTT reaction carried out 3 days after plating of 1,000–50,000 cells in 96 well plates. The color intensity was compared to a standard curve containing variable numbers of control cells. Absorbance at x nm was determined with a BioRad Plate reader. For L1210, growth in fresh medium was allowed to occur during the next 3 days, and cell numbers were similarly estimated using the MTT assay procedure.

(iv) Lipoprotein Binding.

Binding of Pd-BPheid to protein and lipoprotein compound of control human plasma was determined. Incubation of 250 µl plasma sample with 3 µM of the compound for 30 min at 37° C. Lipoprotein and protein components were then separated by density-gradient centrifugator. The gradients were fractionated, fractions diluted into 3 ml of 10 mM Triton X-100 detergent or of fluorescence at 750–800 nm determined upon excitation at 400 nm.

Results (v) Phototoxicity Effect of Pd-BPheid on L1210 Cells.

L1210 murine leukemia cells were incubated with 1 µM Pd-BPheid for 30 min at 37° C. resulting in a 50% cell killing using a 75 mJ/$cm^2$ dose of light at 760±5 nm. A similar degree of cell killing in the RIF line required a 215 mJ/$cm^2$ light dose.

(vi) Phototoxicity Effect of Pd-BPheid on HT29 Cells.

The survival rate varied between 100% and 79% when HT29 cells were incubated with Pd-BPheid without light. The cellular survival rate when the concentration of Pd-BPheid was higher and when the doses of energy delivered were increased. The Pd-BPheid photosensitizer dose causing a 50% death rate (also called $LD_{50}$) was 48 µM under an irradiation of 25 J/$cm^2$. The excitation wavelength inducing the most important phototoxicity was 773 nm.

(vii) Sites of Photodamage.

Using mouse leukemia L1210 cells, Pd BPheid was highly specific mitochondrial photosensitizers with no detectable photodamage to the plasma membrane or to lysosomes. Such a result has been associated with rapid initiation of apoptosis.

(viii) Plasma Lipoprotein Binding.

Studies carried out indicated that Pd-BPheid bound to HDL>LDL>>> Albumin fractions of human serum, considered to be one determinant of PDT selectivity.

Example 6

Formulations of Pd-Bpheid: Solubilization and Stability of Pd-Bpheid in Solvents Used for Animal Experiments Solutions of Pd-BPheid were made up in different formulations to obtain a concentration of 0.05 to 2%.

(a) Cremophor formulation was prepared as follows: 40 mg of Pd-BPheid was dissolved in 2 ml of Cremophor EL in a dry tube either by slow rotation of the vial until the solution had been completely free from particles, or using short pulses of a sonic oscillator probe. The tube was cooled such that temperature did not rise above 30° C. After the drug was solubilized, 0.6 ml of propylene glycol was added and again mixed either by slow rotation or with the sonic probe. Isotonic NaCl was then added in 0.1 ml portions to a total volume of 4 ml. The mixture should be clear after each addition, with no evidence of a precipitate. The compositions were briefly treated with the sonic probe after each addition of NaCl 0.9% taking care to keep the temperature below 25–30° C. The concentration of drug was assessed by measuring the absorbance at 757 nm after dilution into ethanol.

When 20 mg/kg of Pd-BPheid were used in experimental studies, this translated into 0.4 mg per 20 gram mouse. Since no more than 0.1 ml of Cremophor can be injected into a tail vein, the drug concentration was then 4 mg/ml.

(b) A modified Cremophor formulation was prepared as follows: 5 mg of Pd-BPheid was mixed with 0.4 ml of Cremophor EL. After dissolution, 0.12 ml of propylene glycol was added. Isotonic saline (1.48 ml) was then added in small portions, and the same was mixed after each addition. The final solution was completely clear and free from particles. An ultrasonic probe was used to aid in dissolving the drug, keeping the solutions below 25° C. by cooling as needed in an ice bath.

The determination of Pd-BPheid concentration in the Cremophor solution was performed by dilution into methanol. The absorbance spectrum was measured over 740–780 nm. The peak value was compared with the results from a known concentration of Pd-BPheid.

(c) Additional formulations were prepared using Tween 80 and ethanol to solubilize Pd-BPheid (1 mg Pd-BPheid/ml solution).

Example 7

In Vivo Toxicity Studies—Effect of Pd-Bpheid on Murine Tumor Models

Two sets of experiments involving murine tumor models were used to assess the phototoxicity of Pd-Bpheid.

(a) The photodynamic responsiveness of Pd-BPheid was firstly evaluated in two murine tumor models: BA—mammary adenocarcinoma and radiation induced fibrosarcoma (RIF-1)

Photodynamic therapy parameters: Mice with tumors measuring 5–7 mm in diameter were entered into PDT experiments. Three Pd-BPheid drug doses (1, 5 and 10 mg/kg) and two light doses (100 and 300 Joules/sq.cm) were evaluated. A formulation of Pd-BPheid dissolved in Cremophor was administered by i.v. tail injection. PDT light exposure was started either 15 minutes, 1 hour or 4 hours following injection. Three mice were treated under each treatment condition unless initial results demonstrated lethal toxicity or non-responsiveness. A titanium sapphire laser tuned to 757 nm was used as the light source for PDT. Laser generated light was coupled into quartz fibers for delivery of light to tumors. A light power density of 75 mW/sq.cm was used. Tumor size was measured 3 days per week following PDT treatments and the percentage of tumor cures (defined as no tumor recurrence for 40 days post treatment) was determined.

In vivo PDT Response: Tables 4 and 5 hereinafter provide summaries of the PDT treatment results for C3H mice transplanted with either the BA mammary carcinoma or the RIF-1 fibrosarcoma. Each table indicates the following parameters: 1) intravenous drug dose expressed in mg/kg; 2) laser treatment parameters, including the total light dose ($J/cm^2$), the wavelength (757 nm), the light dose rate (mW/$cm^2$), and the time interval (between treated for each group, 4) toxicity (four mice died shortly after treatment), 5) tumor regrowth (consisting of the number of days between PDT treatment and tumor recurrence), and 6) the number of mice (and percentage) with Pd-BPheid PDT induced tumor cures.

As shown herein, Pd-BPheid mediated PDT was found to induce both a classical and an efficient tumoricidal response in two mouse tumor models. PDT mediated tumor responsiveness was directly correlated with drug dose, light dose and time interval between drug administration and light treatment. Specifically, higher drug doses and/or higher light doses produced enhanced responses. The BA mammary carcinoma was found to be more responsive to Pd-BPheid mediated PDT than comparable PDT treatments of the RIF-1 fibrosarcoma. Pd-BPheid mediated PDT was effective when light treatments were initiated within 1 hour of drug administration, and was not effective when a 4-hour interval between drug administration and light treatment was used.

(b) In the second set of experiments, the phototoxicity of Pd-BPheid was assessed in a mouse tumor model transplanted with HT29 human colon adenocarcinoma.

Animal and tumor model: Solid tumor tissue (diameter 2 cm) removed from donor mouse immediately after death was mechanically crushed in 1 ml of 0.9% saline solution and the solution (0.1 ml) was injected s.c. into one hind leg of each mouse. Mice were included for experiments when the tumor diameter was 8–10 mm. Tumors were grafted s.c. in 8-week aged Swiss nude mice 10 days before experiment.

Phototoxic studies: 0.15 ml Pd-BPheid was injected i.v. at 15 mg/kg. Mice were anesthetized with thiopental at 40 mg/kg just before irradiation. At 30 min, 1 h, 4 h or 24 h after injection, mice were irradiated with a titanium sapphire laser at 300 $mW/cm^2$, mean diameter were measured to adjust time irradiation to obtain 200 or 300 $J/cm^2$. Control mice not injected with Pd-BPheid were also irradiated in same conditions. The tumor growth delay induced by PDT was analyzed by equivalence with tests realized in experimental radiotherapy. For in vivo studies and for each separate experiment, all results were the mean of 2 or 3 separate experiments and for each separate experiment, 2 mice were used for each experimental condition.

Concerning tumoral growth studies, results are expressed as tumoral index variations with reference (=1) corresponding to tumoral index from non-treated cells. The tumoral index was calculated as follows:

Tumoral index=(largest tumoral diameter+perpendicularly opposite diameter)/2.

Temperature variation studies: to assure that the thermic effect was not excessive, temperature variation was measured for the halogen lamp and the titanium sapphire laser irradiation using non-absorbing alumin-embedded microthermocouples.

The results of this experiment are the following:

(i) 763 nm Irradiation at 200 $J/cm^2$:

A tumor growth decrease (as compared to controls) was observed for the conditions 30 min and 4 h after injection. A decrease of tumor index was observed up to 7 days for the conditions 1 h and 24 h after injection.

(ii) 763 nm Irradiation at 300 $J/cm^2$:

A tumor growth decrease was observed (as compared to controls) for the conditions 30 min and 24 h after injection. A decrease of tumor index was observed up to 7 days for the conditions 1 h and 4 h after injection.

(iii) 300 $J/cm^2$ Irradiation 1 h After Injection:

A tumor growth decrease was observed (as compared to controls) for the condition 773 nm up to 5 days and for the conditions 753 nm and 763 nm up to 12 days. The maximum tumor growth decrease was observed for 763 nm.

(iv) 300 $J/cm^2$ Irradiation 24 h After Injection:

A tumor growth decrease was observed (as compared to controls) for the condition 753 nm up to 4 days and for the conditions 763 nm and 773 nm up to 12 days. The maximum tumor growth decrease was observed for 773 nm.

No excessive temperature variation was observed during halogen lamp or titanium sapphire irradiation of mice.

In summary of this study, the optimal wavelength of irradiation was found to be 773 nm. The delay between injection and illumination had an influence on the tumor response. At 764 nm, a one hour delay was shown to be the most efficient. When using a 773 nm wavelength, the most efficient delay was 24 hours.

TABLE 4

C3H/BA Mammary Carcinoma Response to Pd-BPheid

| Drug Dose (mg/Kg) | Light Parameters | Number of Animals Treated | Toxicity (Treatment Associated Death) | Number of Animals with Primary Tumor Regrowth (Days to Recurrence) | Summary (cures) % |
|---|---|---|---|---|---|
| 1 i.v. | 300 $J/cm^2$ 757 nm 75 $mW/cm^2$ 15 min interval | 1 | 0 | 1 (1 da) | – no response |

TABLE 4-continued

C3H/BA Mammary Carcinoma Response to Pd-BPheid

| Drug Dose (mg/Kg) | Light Parameters | Number of Animals Treated | Toxicity (Treatment Associated Death) | Number of Animals with Primary Tumor Regrowth (Days to Recurrence) | Summary (cures) % |
|---|---|---|---|---|---|
| 5 i.v. | 300 J/cm² 757 nm 75 mW/cm² 15 min interval | 3 | 0 | | + 1 (41 days) 2 (40 days) 100% |
| 5 i.v. | 300 J/cm² 757 nm 75 mW/cm² 1 hr interval | 3 | 0 | 1 (11 days) | + 2 (41 days) 66.6% |
| 10 i.v. | 300 J/cm² 757 nm 75 mW/cm^w 1 hr interval | 3 | 0 | | + 2 (41 days) 1 (41 days) 100% |
| 10 i.v. | 300 J/cm² 757 nm 75 mW/cm² 4 hr interval | 2 | 0 | 2 (1 day) | − no response |
| 10 i.v. | 100 j/cm² 757 nm 75 mW/cm² 15 min interval | 3 | 0 | | + 2 (42 days) 1 (41 days) 100% |
| 10 i.v. | 100 J/cm² 757 nm 75 mW/cm² 1 hr interval | 3 | 0 | 1 (5 days) | + 2 (40 days) 66.66% |

TABLE 5

RIF-1 Response to Pd-BPheid

| Drug Dose (mg/Kg) | Light Parameters | Number of Animals Treated | Toxicity (Treatment Associated Death) | Number of Animals with Primary Tumor Regrowth (Days to Recurrence) | Summary (cures) % |
|---|---|---|---|---|---|
| 1 i.v. | 300 J/cm² 757 nm 75 mW/cm² 15 min interval | 2 | 0 | 2 (1 da) | − no response |
| 5 i.v. | 300 J/cm² 757 nm 75 mW/cm² 15 min interval | 3 | 0 | 1 (5 days) 1 (12 days) | + 1 (40 days) 33.33% |
| 5 i.v. | 300 J/cm² 757 nm 75 mW/cm² 1 hr interval | 3 | 0 | 1 (4 days) 1 (2 days) 1 (7 days) | + |
| 10 i.v. | 300 J/cm² 757 nm 75 mW/cm^w 15 interval | 3 | 2 2 (1 day) | | + 1 (41 days) 33.33% |
| 10 i.v. | 300 J/cm² 757 nm 75 mW/cm^w 1 hr interval | 3 | 2 2 (1 day) | | + 1 (41 days) 25% |

TABLE 5-continued

RIF-1 Response to Pd-BPheid

| Drug Dose (mg/Kg) | Light Parameters | Number of Animals Treated | Toxicity (Treatment Associated Death) | Number of Animals with Primary Tumor Regrowth (Days to Recurrence) | Summary (cures) % |
|---|---|---|---|---|---|
| 10 i.v. | 300 J/cm² 757 nm 75 mW/cm² 4 hr interval | 1 | 0 | 2 (1 day) | – no response |
| 10 i.v. | 100 j/cm² 757 nm 75 mW/cm² 15 min interval | 3 | 0 | 2 (12 days) 1 (7 days) | + |
| 10 i.v. | 100 J/cm² 757 nm 75 mW/cm² 1 hr interval | 3 | 0 | 2 (3 days) 1 (6 days) | + |

Example 8

Morphological Evaluation of A431 Human Epithelial Carcinoid Cells after Pd-BPheid and BChl-Ser Based PDT This experiment was performed in order to examine the time-dependent morphological changes occurring after PDT with Pd-BPheid or BChl-SerOMe on A431 human epithelial carcinoid cells.

(i) Materials:

The Pd-BPheid was prepared as in Example 1 above and the serine methyl ester BChl-SerOMe was prepared as in EP 584552.

(ii) Light Source:

Halogen lamp (Osram, Germany, 100 W), with 4.5 cm water filter and cut off filter >650 nm. The cells were illuminated for 10 minutes, 15 mW/cm2, a total energy fluency of 9 J/cm². For illumination, the culture plates were placed on a glass table to provide the light from the bottom.

(iii) Phototoxicity Study:

A431 cells (5×104 cells) were seeded in 3 cm dishes in duplicates and cultured to 75% confluency in Dulbecco's modified Eagle's medium (DMEM)+F12 (1:1), buffered with HEPES (25 mM, pH 7.4), fetal calf serum (FCS) with penicillin (0.06 mg/ml) and streptomycin (0.1 mg/ml). Pd-BPheid or BChl-Ser were added to the cells at the corresponding LD90 concentration (0.1 and 1 µM, respectively). After a 4-hour period the cells were washed with culture medium and the cells were illuminated with the light source above. Phase contrast microscopic examination was performed at different time points after illumination (0, 0.5, 4 and 24 hours post-PDT) using Zeiss Axiovert-35 light microscope (magnification ×320) equipped with a Contax 35 mm SLR camera. In the second dish of every duplicate, cell viability was assessed 24 hours post-PDT using neutral red viability assay (Zhang SZ., 1990, *Cell Biol Toxicol* 6(2): 219–234).

Figure 4:
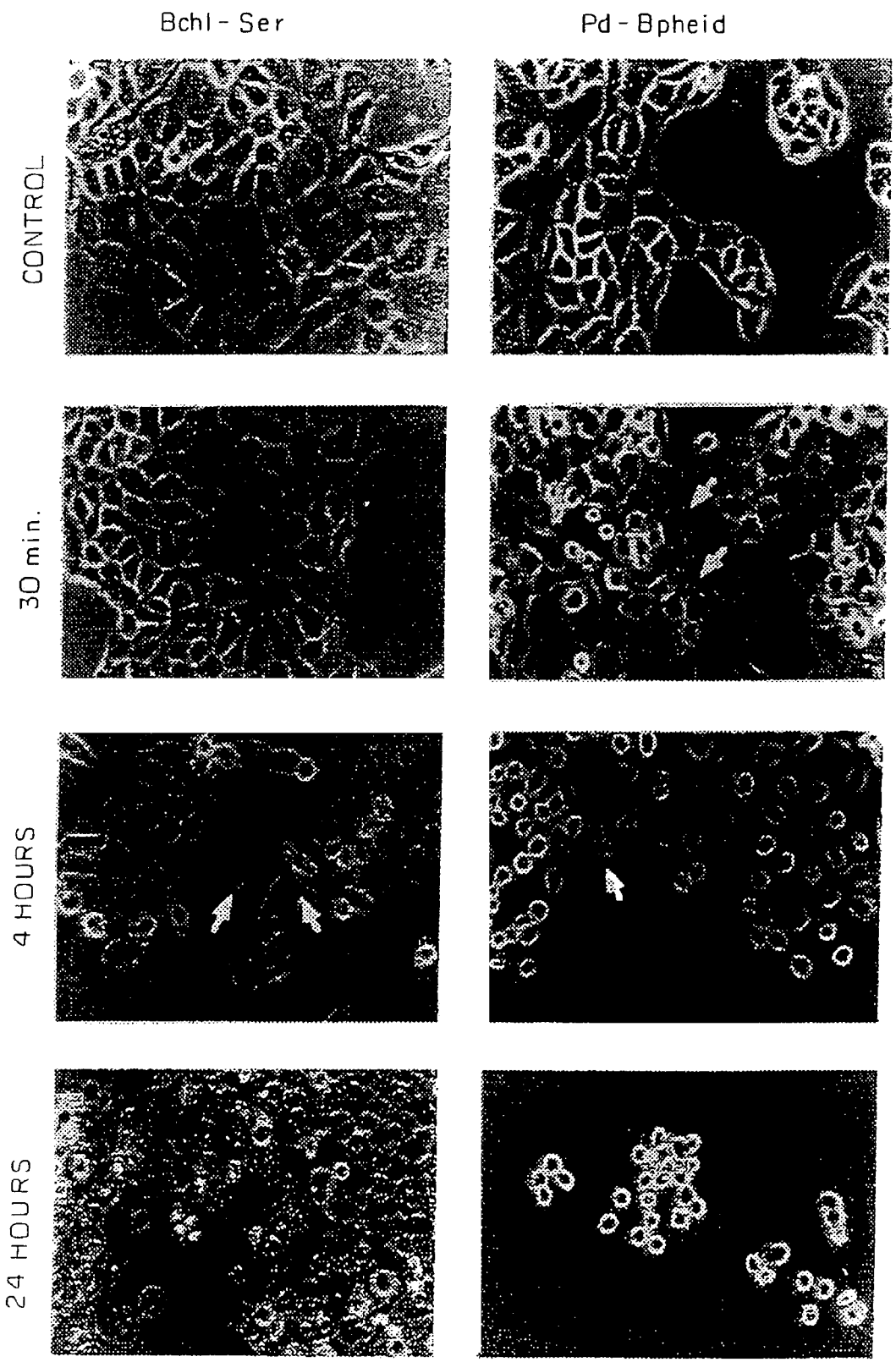
FIG. 4 shows time-dependent morphological changes of A431 cells with Pd-BPheid or BChl-SerOMe post PDT. (In the Figures, Bchl-Ser stands for BChl-SerOMe, the seryl methyl ester of BChl.)

(iv) Results:

Both sensitizers caused significant changes in the cell morphology. Pd-BPheid caused a fast alteration in the cells membrane structure (30 minutes), the cells rapidly shrinked and fibrous connections were formed, connecting the cells membrane with the original focal adhesion points (fibrous phenotype). After 4 hours, 90% of the cells lost most qf their inner volume and a large portion of them detached from the dish, no further change was observed after 24 hours (FIG. 4, right column). Bchl-Ser showed a different pattern of time dependant morphological changes that could be observed only after 4 hours. Membrane blabbing was seen as dark vesicles budding out from the cells membrane. No significant volume decrease was observed over 24 hours and after this period most of the cells were attached to the dish but appeared hollow (blabbing phenotype, FIG. 4, Left column). Twenty four hours after illumination, neutral red viability assay was performed which confirmed 90±7% cell killing in both of the experimental groups. In FIG. 4, the fibrous phenotype is represented in the right column and the blabbing phenotype is represented in the left column. The solid white arrows show the formations of the fibers or the blabs.

Example 9

Photocytotoxicity of Pd-BPheid and BChl-SerOMe on the Human Bladder Carcinoma Cell Line ECV304

This experiment was carried out for assessing the photocytotoxic effects of the photosensitizers Pd-BPheid and BChl-SerOMe on ECV304 human bladder carcinoma cells.

(i) Materials:

As in Example 8(i).

(ii) Light Source:

As in Example 8(ii).

(iii) Phototoxicity Study:

ECV304 cells (2×10⁴ cells per well) were cultured in M-199, 10% FCS with penicillin (0.06 mg/ml) and streptomycin (0.1 mg/ml) in 96-well to confluence (~2×10$^5$ cells per well). Incubation with increasing concentrations of Pd-BPheid or BChl-SerOMe with the cells for 4 hours was followed by washing with fresh culture medium and illumination as described above Sec. 1. Twenty-four hours after illumination, cell viability was assessed using neutral red viability assay. The following controls were used: Light Control: irradiated cells, not treated with sensitizer; Dark Control: non-irradiated cells, treated with sensitizer in the dark; Untreated Control: cells not treated with sensitizer and unirradiated were used for calculation of 100% survival (Rosenbach-Belkin V. et al., 1996, *Photochem Photobiol* 64(1):174–181)

Figure 5:
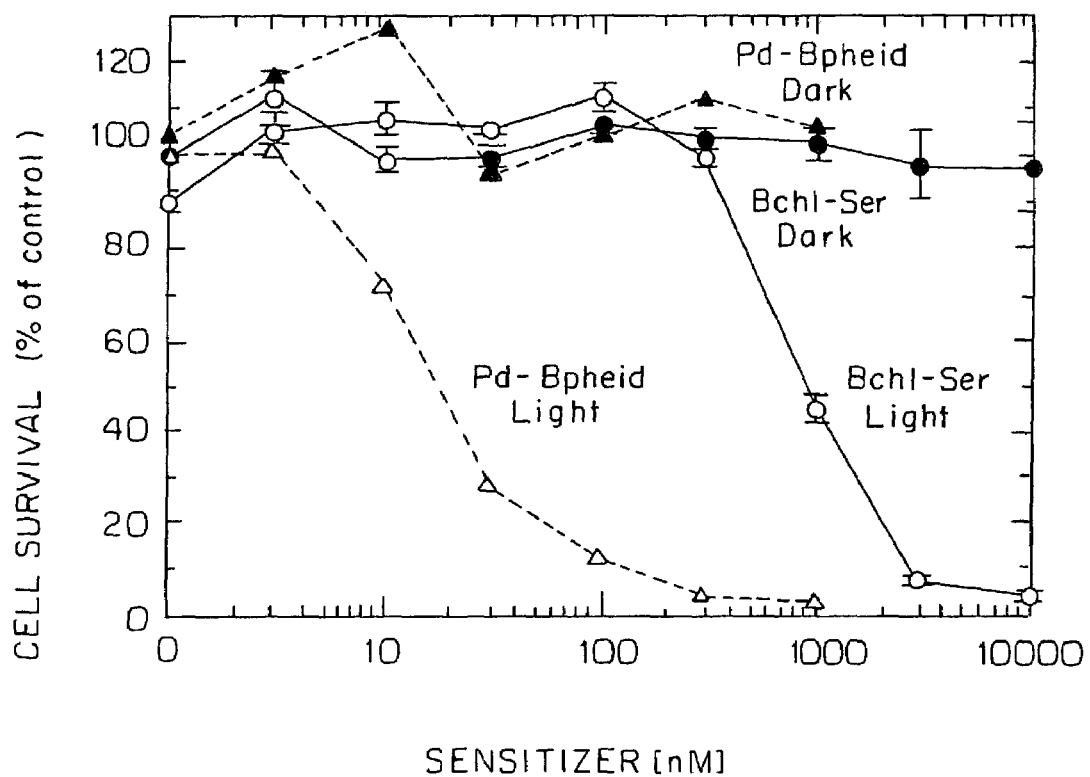
FIG. 5 shows phototoxicity of Pd-BPheid and BChl-SerOMe tested on ECV-304 cells.

(iv) Results:

Both Pd-BPheid and BChl-SerOMe exhibited dose and light dependent cytotoxicity on ECV304 cells (FIG. 5). The corresponding $LD_{50}$ values are 19 and 1000 nM. Morphological changes post-PDT were consistent with the observations made with A431 cells (data not shown).

Example 10

PDT of Pd-BPheid and Pd-BPheid-ethyl Ester on M2R Mouse Melanoma Cells

The aim of this experiment was to test the effect of Pd-BPheid and Pd-BPheid-ethyl ester on M$_2$R cells.

(i) Materials:

Pd-Bpheid was prepared as in Example 1 above and the Pd-Bacteriopheophorbide a ethyl ester (Pd-Bpheid-ethyl ester) was prepared as described in WO 97/19081.

(ii) Light Source:

As above in Example 8(ii) but cells were illuminated for 10 minutes, 12 mW/cm$^2$, a total energy fluency of 7 J/cm$^2$.

(iii) Phototoxicity Study:

M$_2$R cells were cultured as monolayers in Dulbecco's modified Eagle's medium (DMEM)+F12 (1:1), buffered with HEPES (25 mM, pH 7.4). Fetal bovine serum (FBS) (10%), glutamine (2 mM), penicillin (0.06 mg/ml) and streptomycin (0.1 mg/ml) were included and the cells were grown at 37° C. in a humidified atmosphere containing 8% CO$_2$. For phototoxicity analysis cells (1×10$^4$ cells/well) were cultured in 96-well plates for 24 hours to an approximate density of 2×10$^4$ cells/well. Pigments were dissolved directly in culture medium or in ethanol 95% and further diluted in culture medium to a final concentration of 1% ethanol. The diluted pigments were added and the cells were incubated in the dark for four hours at 37° C. Prior to illumination, the cells were washed once and replaced with fresh culture medium. The plates were then illuminated from the bottom for 10 minutes at room temperature and placed in the culture incubator at 37° C. in the dark. Cell survival was determined 24 hours later. The following control systems were used: Dark Control: untreated cells kept in the dark; Light Control: cells not treated with sensitizer that were illuminated; Dark Toxicity: cells treated with pigment but kept in the dark. Cell survival was determined by [$^3$H]-thymidine incorporation as described earlier (WO 97/19081).

Figure 6A:
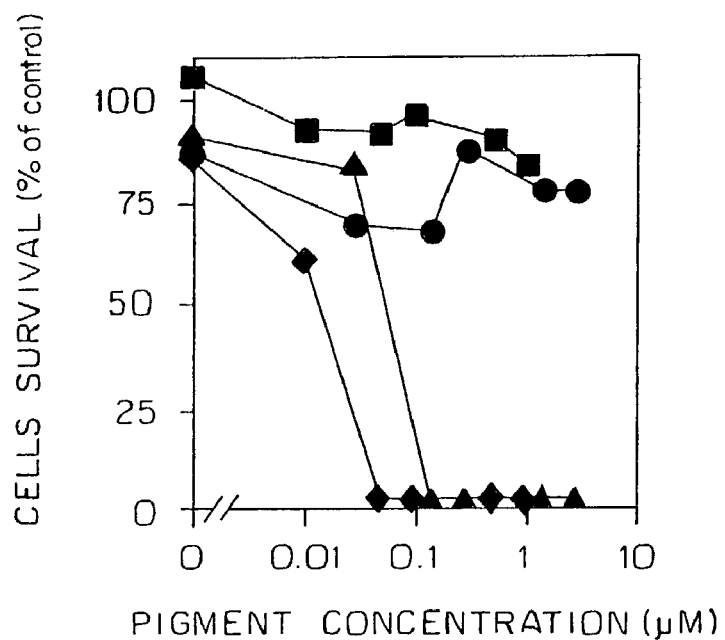
FIG. 6 shows phototoxicity of Pd-BPheid and Pd-BPheid-ethyl ester on cultured M2R mouse melanoma cells. (A) pigments dissolved in 95% ethanol and further diluted to the indicated concentrations in culture medium+10% serum to 1% ethanol. (B) pigments dissolved directly in culture medium+10% serum.
Figure 6B:
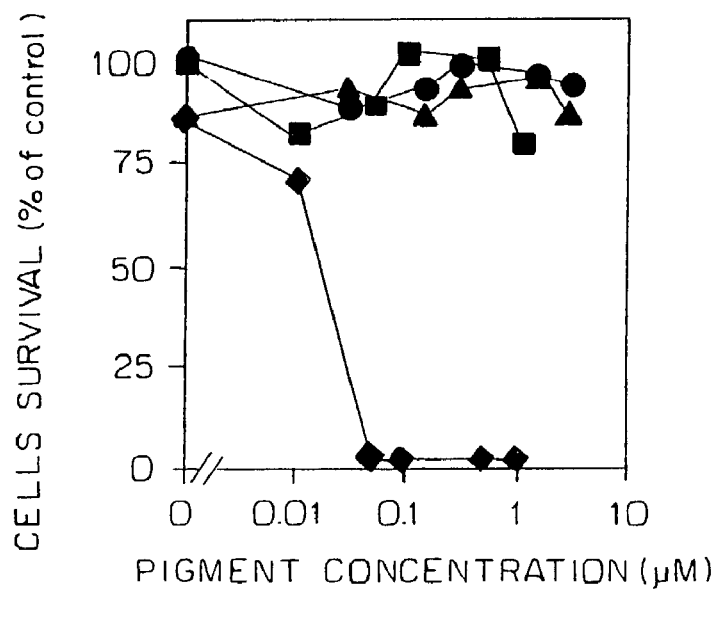

(iv) Results:

As can be seen in FIG. 6A, when the pigments were dissolved in ethanol 95%, Pd-BPheid had a $LD_{50}$ of 0.03 µM, while the Pd-BPheid-ethyl ester had a $LD_{50}$ of 0.07 µM. When the pigments were dissolved directly in culture medium containing 10% serum, only the Pd-BPheid was fully active while the Pd-BPheid-ethyl ester was not active at all up to 1 µM, the highest concentration tested (FIG. 6B).

Example 11

PDT of Pd-BPheid on M2R Mouse Melanoma and Human HT29 Colon Carcinoma Cells

These experiments were aimed at determining the phototoxic effect of Pd-BPheid toward two cell lines: M2R mouse melanoma and human HT29 colon carcinoma cells.

(i) Materials:

Pd-Bpheid was prepared as in Example 1 above.

(ii) Light Source:

The light source was a Xenon fluorine LS3-PDT lamp (Bio-Spec, Russia), with 10 cm water filter and 720–850 nm light band. The cells were illuminated for 10 minutes, 12 mW/cm$^2$, at a total energy of 7 J/cm$^2$.

(iii) Phototoxicity Study:

Analysis was performed with the same protocol as described above (Example 10) with the following changes: Pd-BPheid was dissolved directly in medium containing 10% serum and then added to the cells. Survival of M2R cells was determined by [$^3$H]-thymidine incorporation and that of human HT29 cells with the MTT assay (Merlin J L et al., 1992 *Eur J Cancer* 28A:1452–1458).

Figure 7A:
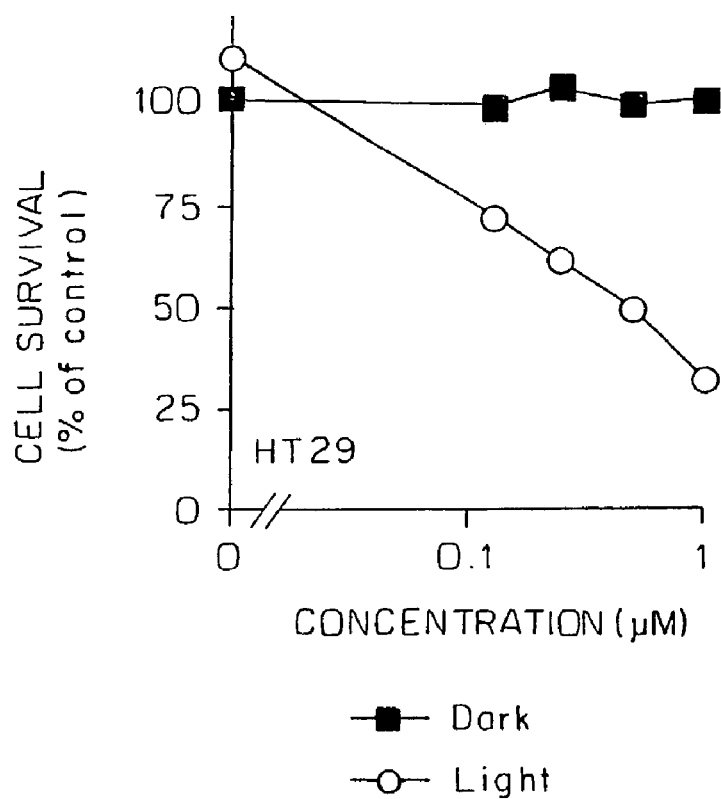
FIG. 7 shows phototoxicity of Pd-BPheid on cultured M2R mouse melanoma and human H29 colon carcinoma cells.
Figure 7B:
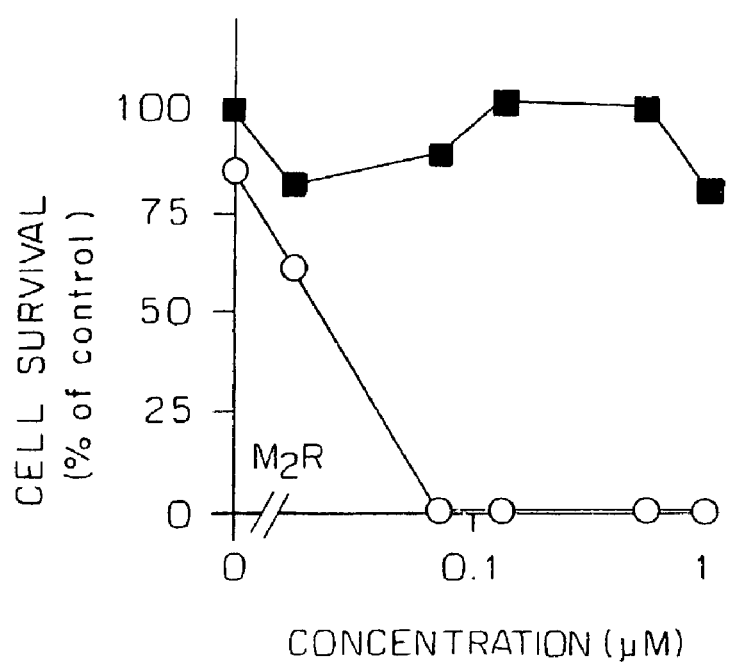

(iv) Results:

As can be seen in FIG. 7, human colon HT-29 cells show lower sensitivity toward this pigment ($LD_{50}$ of 0.5 µM), while the M$_2$R cells were about 10 times more sensitive ($LD_{50}$ of 0.03 µM).

Example 12

In Vivo PDT of M2R Mouse Melanoma Tumors with Pd-BPheid

The aim of this experiment was to study PDT of M2R mouse melanoma tumors in CD1 nude mice with 2.5 mg/Kg Pd-Bpheid.

(i) Materials:

P d-Bpheid was prepared as in Example 1 above.

(ii) Mice:

C D1 nude mice (25–30 g)

(iii) Anesthesia:

i.p injection of 50 µl of Ketamine/Rumpon (vol/vol=85/15).

(iv) Tumor Implantation:

Mice were implanted with 106 M2R cells on the back and tumors arose to the treatment size (7–8 mm) within 2–3 weeks.

(v) Light Source:

Osram150 W halogen photo-optic lamp 64643 (D. K. Keller et al 1999, *Int J Hyperthermia* 15:467–474) equipped with λ=650–900 mn spectral window, 300 mW/cm-2. Illumination was for 30 min.

(vi) PDT Protocol:

The anesthetized mouse was i.v injected with the pigment and the tumor immediately illuminated. At the end of treatment the mouse was placed back in the cage. Photographs of the tumor were taken before and at the times indicated.

Experiment 1

Preparation of Sensitizer:

Two mg Pd-BPheid were dissolved in 0.25 ml Cremophor EL followed by 20 min sonication. 0.075 ml 1,2-propylene glycol were added and sonication was continued for another 15 min. Then 0.9 ml of 0.15 mM NaCl were added followed by 5 min sonication. The sample was centrifuged for 12 min at 13,000 rpm (Eppendorf). The final calculated concentration of Pd-BPheid based on spectrum in chloroform was 0.5 mg/ml.

Figure 8:
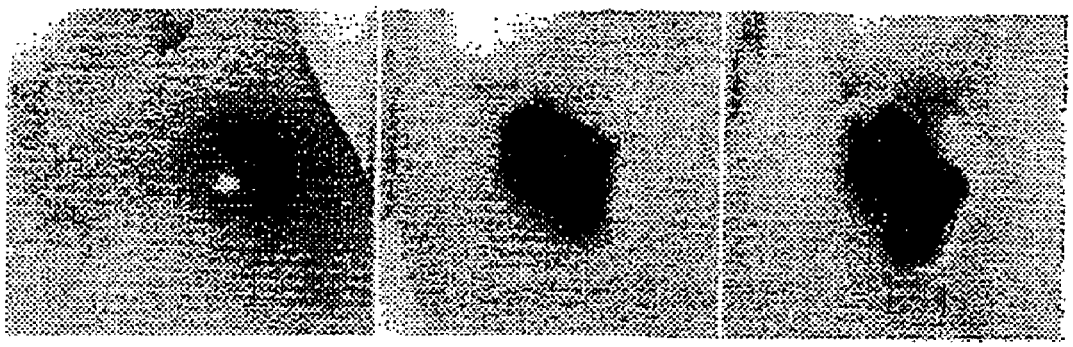
FIG. 8 shows PDT of M2R mouse melanoma with Pd-BPheid (2.5 mg/Kg) dissolved in Cremophor and diluted in salt solution.

PDT of Tumor:

Pd-BPheid 2.5 mg/kg was i.v injected to CD1-Nude mouse bearing M2R melanoma tumor. The tumor was illuminated for 30 min at 300 mW cm$^{-2}$. The temperature of the mouse skin tumor area was 37.7–38° C. The response of tumor was followed 1 and 4 days after treatment. The results are shown in FIG. 8.

Experiment 2

Preparation of Sensitizer:

Two mg Pd-BPheid were dissolved in 0.1 ml methanol, 0.1 ml 0.1 M $KH_2 PO_4$, pH=8.0 and 0.9 ml PBS and sonicated for 10 min. The methanol was evaporated with Argon and 20% of Cremophor EL: 1,2-propylene glycol (3:1) was added following by 15 min sonication. The sample was centrifuged for 8 min on 13,000 rpm the final calculated concentration of Pd-BPheid based on spectrum in chloroform was 0.5 mg/ml.

PDT of Tumor:

Pd-BPheid 2.5 mg/kg (120 μl) was i.v administered to CD1-Nude mice bearing M2R melanoma tumor. The tumor tissue was illuminated for 30 min at 300 mW cm$^{-2}$. The temperature of the mouse skin tumor area was 37.7–38° C. The response of tumor was followed 1 and 4 days after treatment. The results are shown in FIG. 9.

Results

Figure 9:
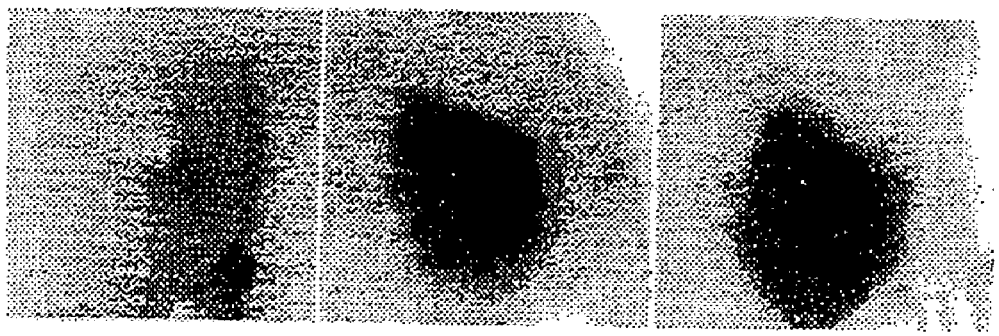
FIG. 9 shows PDT of M2R mouse melanoma with Pd-BPheid (2.5 mg/Kg) dissolved in salt solution and diluted with Cremophor.

As shown in FIGS. 8 and 9, PDT of M2R melanoma tumors with 2.5 mg/Kg Pd-Bpheid as described above induces severe inflammatory response with necrosis of the tumor within 24 h.

Example 13

Pd-BPheid Based PDT Reduces Rate of C6 Glioma Metastasis Formation in Mice: Advantage over Surgery These experiments were conducted in order to compare the therapeutic potential of Pd-BPheid and BChl-SerOMe based PDT, and the probability of metastasis spread by Pd-BPheid and BChl-SerOMe based PDT.

(i) Materials:

Pd-BPheid (prepared as in Example 1) or Pd-BPpheid-SerOMe 5 mg/kg in 20% Cremophor EL.

(ii) Light Source:

The light source was a Xenon fluorine LS3-PDT lamp (Bio-Spec, Russia), with 10 cm water filter and 720–850 nm light band.

(iii) Mice:

CD1 nude mice.

(iv) Tumors:

Mice were implanted with $10^6$ C6 glioma cells in the foot of the hind leg. Tumors were treated when reached a length of 7–8 mm.

(v) Anesthesia:

50 μl of Vetalar/Rumpon (vol/vol=85/15).

(vi) Analgesia:

Oxycodone (12 mg/liter) added in 5% sucrose drinking water, as of treatment (amputation or PDT) for one week.

(vii) Protocol:

Three groups (10 mice in each) were i.v. injected with 5 mg/Kg of sensitizer (Pd-BPheid or Pd-BPpheid-SerOMe) and immediately illuminated at 200 mw/cm$^2$, for 30 minutes, and the animals were allowed to recover in the cage.

Groups 1 and 2:

Animals which received PDT Pd-Bpheid and Pd-BPpheid-SerOMe, respectively. Tumor response and metastasis formation in groin were followed for 4 weeks.

Group 3:

Animals which were amputated at the ankle joint (paired with group 1) and metastasis formation in groin was followed for 4 weeks. The parameters of response to PDT were the percent of animals with tumor necrosis and disappearance, out of the total number of treated animals. Metatstasis was manifested by appearance of tumors in the groin or elsewhere. The endpoints considered were: follow up for 4 weeks, spontaneous death, tumors reached a diameter of 2 cm, metastasis, whichever came first.

Figure 10:
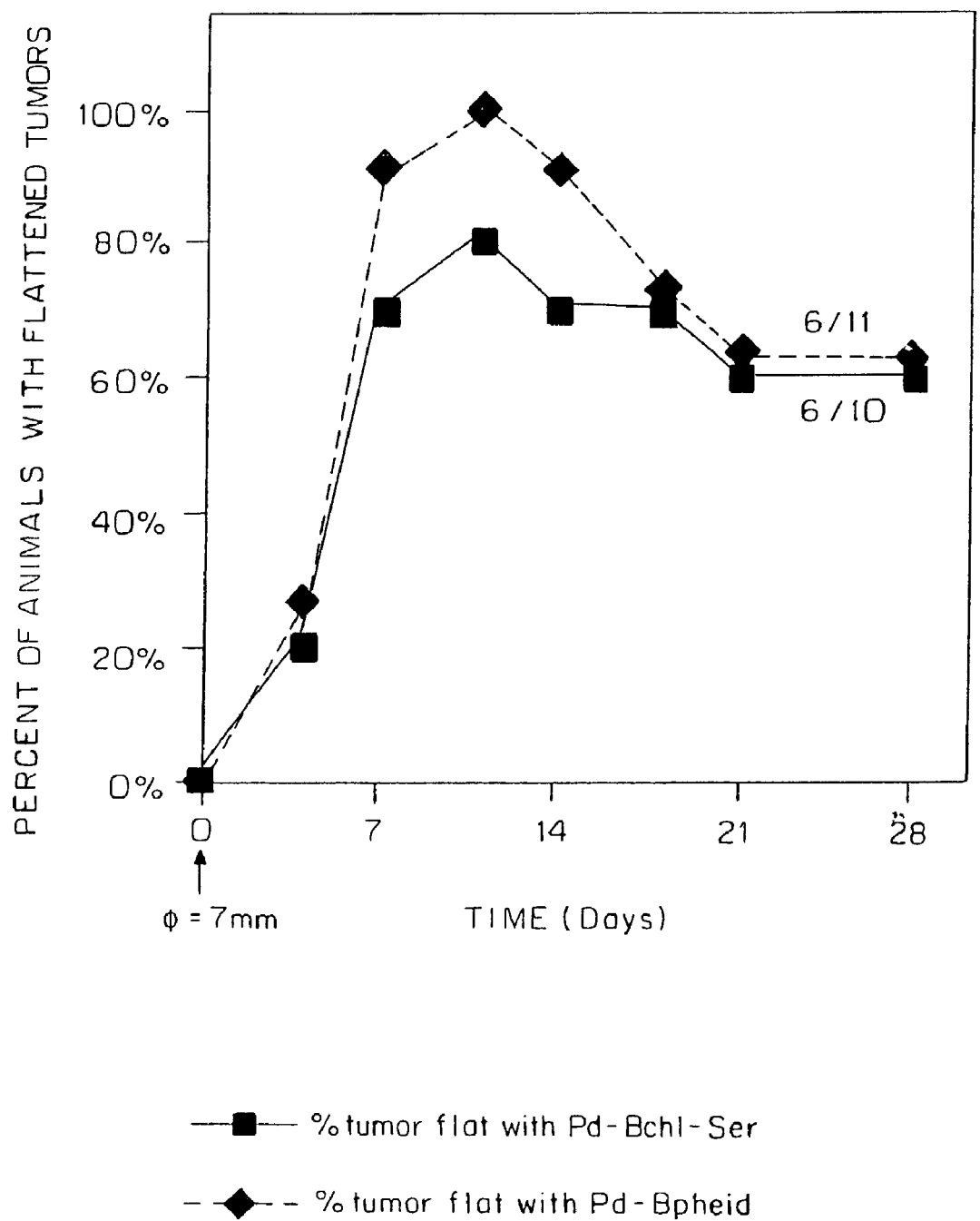
FIG. 10 illustrates cure of primary C6 glioma tumors after PDT with Pd-BPheid or Pd-BPheid-SerOMe (in the Figure, Pd-Bchl-Ser).

(viii) Results:

The results of tumor flattening (disappearance) are shown on FIG. 10. While on day 11 the response to Pd-BPheid was stronger than to Pd-BPheid-SerOMe (100% and 80% tumor flattening, respectively), later, on day 28, the percent of response was similar, about 60%. The decline in tumor flattening in the long term is due to some tumor re-growth in some of the treated animals, probably due to mismatch of light field and tumor area.

Figure 11:
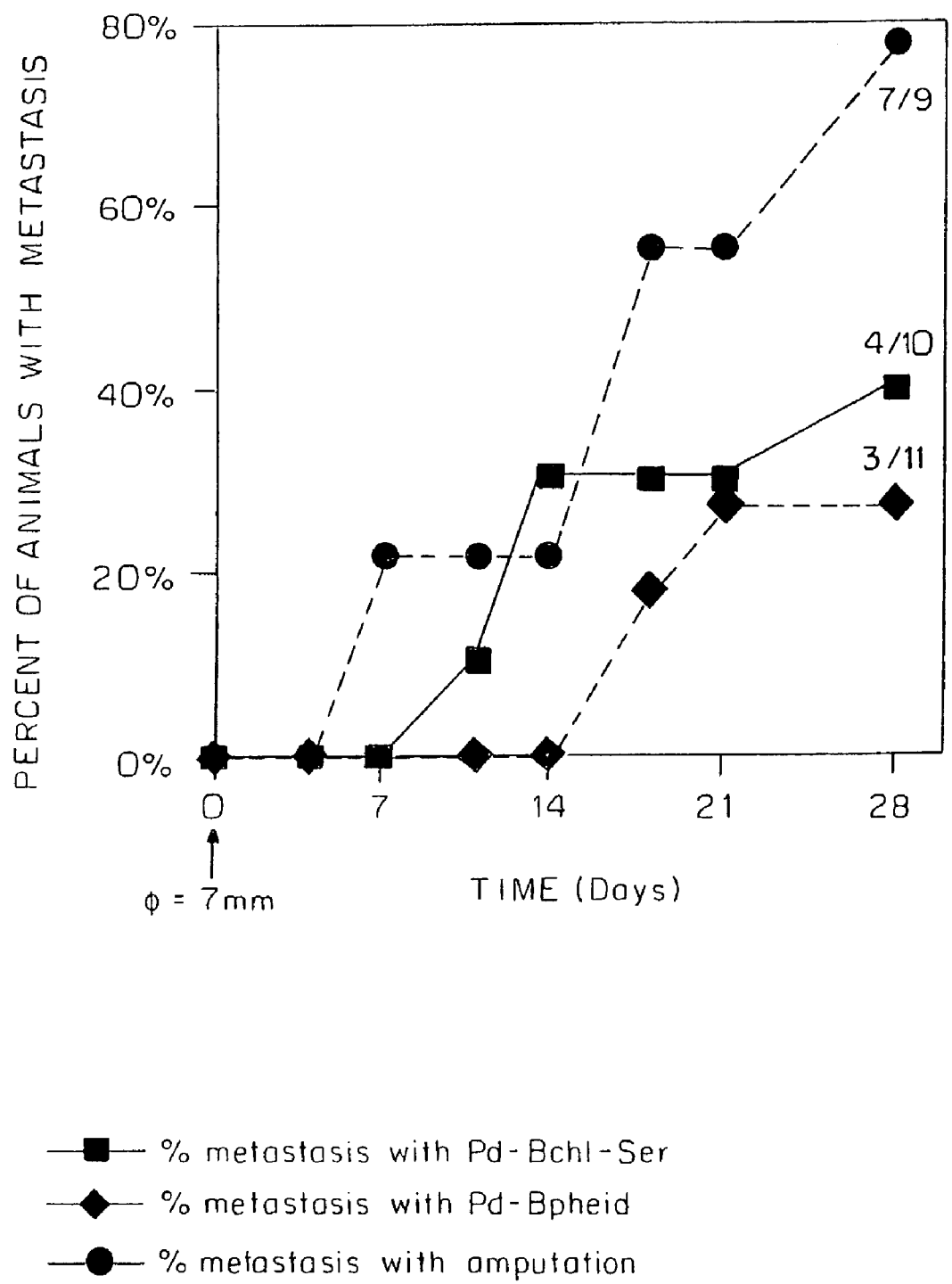
FIG. 11 shows appearance of C6 glioma metastases in CD1 nude mice after surgery (amputation) or after PDT with Pd-BPheid or Pd-BPheid-SerOMe (in the Figure, Pd-Bchl-Ser).

The results of metastasis appearance are shown in FIG. 11. The surgical treatment by leg amputation yielded a substantially higher percent of metastasis in comparison to PDT (up to 78%). In addition, the metastasis after amputation appeared much earlier. The frequency of metastasis after PDT with Pd-BPheid was the lowest (up to 23%). This result is similar to that obtained with Pd-BPheid-SerOMe and the main advantage of Pd-BPheid is delay of metastasis appearance. PDT with Pd-BPheid or Pd-BPheid-SerOMe are curative for C6 glioma tumors. Metastasis formation after PDT is substantially lower when compared with surgical treatment.

What is claimed is:

1. A method for tumor diagnosis which comprises:
   (a) administering to a subject suspected of having a tumor, a compound of the formula I, I' or I"

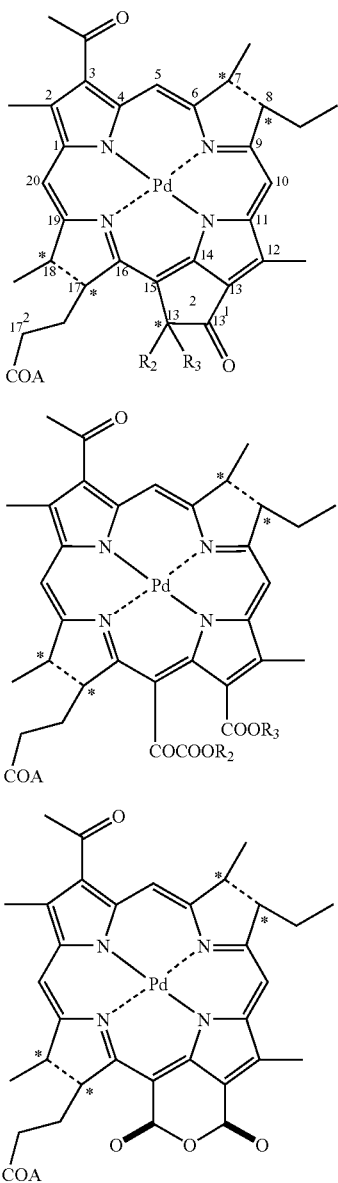

wherein
A represents OH,
$OR_1$,
—O—$(CH_2)_n$—Y,
—S—$(CH_2)_n$—Y,
—NH—$(CH_2)_n$—Y,
—O—$(CH_2)_2$—$NH_2$,
—O—$(CH_2)_2$—OH,
—NH—$(CH_2)_2$—NH—BOC or
—N—$(CH_2$—CH=$CH_2)_2$ wherein
$R_1$ represents $Na^+$, $K^+$, $(Ca^{2+})_{0.5}$, $(Mg^{2+})_{0.5}$, $Li^+$, $NH_4^+$ $^+NH_3$—C $(CH_2OH)_3$, $^+NH_3$—$CH_2$—$(CHOH)_4$—$CH_2OH$, $^+NH_2(CH_3)$—$CH_2$—$(CHOH)_4$—$CH_2OH$ or $^+N(C_nH_{2n'+1})_4$;

$R_2$ represents H, OH or $COOR_4$, wherein $R_4$ is $C_1$–$C_{12}$ alkyl or $C_3$–$C_{12}$ cycloalkyl;

$R_3$ represents H, OH or $C_1$–$C_{12}$ alkyl or alkoxy;

n is 1, 2, 3, 4, 5 or 6,

Y is —$NR'_1R'_2$ or —$^+NR'_1R'_2R'_3$, $X^-$ wherein $R'_1$, $R'_2$ and $R'_3$ independently from each other represent —$CH_3$ or —$C_2H_5$;

X is F, Cl, Br or I, n' is 1, 2, 3 or 4, and wherein ★ denotes an asymmetric carbon and— represents a single saturated bond or a double unsaturated bond; and (b) irradiating the subject by standard procedures and measuring the fluorescence of the suspected area, wherein a higher fluorescence indicates tumor sites.

2. A method according to claim 1 which comprises administering a compound I of the formula and optical configuration as indicated below:

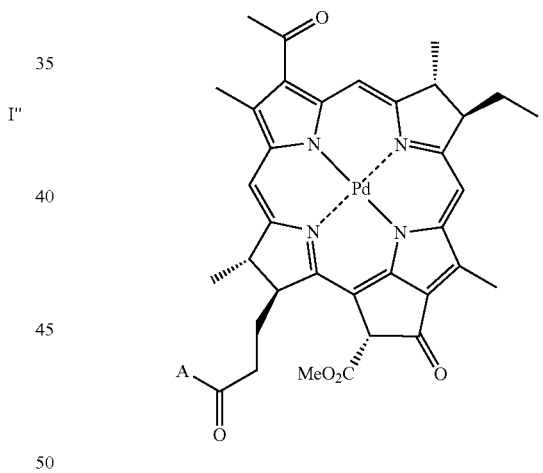

wherein A is OH or $OR_1$, and $R_1$ is as defined in claim 1.

3. The method according to claim 2 which comprises administering the compound wherein A is OH, herein identified as Pd-Bacteriopheophorbide a (Pd-BPheid).

* * * * *